(12) United States Patent
Ino et al.

(10) Patent No.: US 11,186,826 B2
(45) Date of Patent: Nov. 30, 2021

(54) CELL POPULATION INCLUDING MESENCHYMAL STEM CELLS AND PRODUCTION METHOD THEREFOR, AND PHARMACEUTICAL COMPOSITION

(71) Applicant: KANEKA CORPORATION, Osaka (JP)

(72) Inventors: Keita Ino, Hyogo (JP); Yuta Kita, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 162 days.

(21) Appl. No.: 16/590,918

(22) Filed: Oct. 2, 2019

(65) Prior Publication Data

US 2020/0040305 A1    Feb. 6, 2020

Related U.S. Application Data

(63) Continuation-in-part of application No. PCT/JP2018/014326, filed on Apr. 3, 2018.

(30) Foreign Application Priority Data

Apr. 3, 2017  (JP) .............................. JP2017-073984

(51) Int. Cl.
   *C12N 5/077*   (2010.01)
   *C12N 5/0775*  (2010.01)
   *A61K 9/00*    (2006.01)
   *A61K 35/28*   (2015.01)

(52) U.S. Cl.
   CPC .......... *C12N 5/0668* (2013.01); *A61K 9/0019* (2013.01); *A61K 35/28* (2013.01); *C12N 2501/734* (2013.01)

(58) Field of Classification Search
   None
   See application file for complete search history.

(56) References Cited

U.S. PATENT DOCUMENTS 8,961,956 B2 * 2/2015 Kimbrel .............. A61K 35/28
                                                424/93.7
2016/0228474 A1   8/2016 Yamahara et al.

FOREIGN PATENT DOCUMENTS

| JP | 2010/500047    | * | 1/2010 |
|----|----------------|---|--------|
| JP | 2010-500047 A  |   | 1/2010 |
| JP | 2015/500810    | * | 1/2015 |
| JP | 2015-500810 A  |   | 1/2015 |
| JP | 2015-61520 A   |   | 4/2015 |
| WO | WO 2008/020815 A1 | | 2/2008 |
| WO | WO 2013/077428 A1 | | 5/2013 |
| WO | WO 2013/082543 A1 | | 6/2013 |

OTHER PUBLICATIONS

International Search Report, issued in PCT/JP2018/014326, PCT/ISA/210, dated Jul. 10, 2018.
Written Opinion of the International Searching Authority, issued in PCT/JP2018/014326, PCT/ISA/237, dated Jul. 10, 2018.

* cited by examiner

*Primary Examiner* — Ralph J Gitomer
(74) *Attorney, Agent, or Firm* — Birch, Stewart, Kolasch & Birch, LLP

(57) ABSTRACT

An object of the present invention is to provide a cell population comprising mesenchymal cells having low cell aggregability, which is useful for intravenous administration of a cell preparation, and a method for producing the same, and a pharmaceutical composition comprising the cell population. Also provided are methods for producing a cell population comprising mesenchymal stem cells, the method comprising obtaining a cell population having the following cell characteristics (the cell population satisfies the relative expression level of COL11A1 gene to the expression level of SDHA gene of 6.0 or less and the relative expression level of COL16A1 gene to the expression level of SDHA gene of 1.5 or less).

10 Claims, 2 Drawing Sheets

CELL POPULATION INCLUDING MESENCHYMAL STEM CELLS AND PRODUCTION METHOD THEREFOR, AND PHARMACEUTICAL COMPOSITION

CROSS REFERENCE TO RELATED APPLICATIONS

This application is a Continuation-in-Part of PCT International Application No. PCT/JP2018/014326, filed on Apr. 3, 2018, which claims priority under 35 U.S.C. 119(a) to Patent Application No. 2017-073984, filed in Japan on Apr. 3, 2017, all of which are hereby expressly incorporated by reference into the present application.

TECHNICAL FIELD

The present invention relates to a method for producing a cell population comprising mesenchymal stem cells. The present invention further relates to a cell population comprising mesenchymal stem cells and a pharmaceutical composition comprising the cell population.

BACKGROUND ART

Mesenchymal stem cells, also called mesenchymal stromal cells, are somatic stem cells reported to exist in the bone marrow, adipose tissues, tooth pulp and the like. Recently, it has been revealed that these cells also exist in fetal appendages including the placenta, umbilical cord, and fetal membrane. Since mesenchymal stem cells are capable of differentiating into bones, cartilage, and fats, etc., mesenchymal stem cells have been gaining attention as a promising cell source in regenerative medicine.

In addition, since mesenchymal stem cells have immunosuppressive capacity as well as differentiation capacity, it has been reported that intravenous administration thereof enables treatment of immune-related diseases, inflammatory diseases and the like.

Patent Literature 1 describes a method for producing an amniotic mesenchymal cell composition, a method for cryopreserving the composition, and a therapeutic agent. Particularly, this literature discloses that cryopreserved amniotic mesenchymal cells can be produced as a cell preparation optimized for transplantation, by cryopreserving a mixture comprising amniotic mesenchymal cells in a solution containing 5 to 10% by mass of dimethyl sulfoxide and containing 5 to 10% by mass of hydroxyethyl starch or 1 to 5% by mass of dextran.

Patent Literature 2 describes a method for preparing an amniotic mesenchymal stem cell population, comprising the steps of: (D) collecting a cell population of mesenchymal cells from the amnion of a mammal; (E) inoculating the collected cell population at a cell concentration of 400 to 35000 cells/cm$^2$, followed by initial culture for 2 to 3 days; (F) inoculating the cultured cells at 1/5000 or more and less than 1/10 of the cell concentration of the initial culture, and repeating subculture three to four times with medium replacement twice a week; and (G) maintaining the culture of the cells in the same culture dish until confluence when a colony of cells having a fusiform shape is formed in the subculture.

In Patent Literature 3, proteome analysis of human mesenchymal stem cells has confirmed that human mesenchymal stem cells secrete COL11A1 and COL16A1.

CITATION LIST

Patent Literatures

Patent Literature 1: JP Patent Publication (Kokai) No. 2015-61520 A
Patent Literature 2: International Publication No. WO2013/077428
Patent Literature 3: JP Patent Publication (Kohyo) No. 2010-500047 A

SUMMARY OF INVENTION

Technical Problem

In recent years, it has been found that mesenchymal stem cells derived from a fetal appendage are a heterogeneous cell population comprising various cells having different differentiation capacities, proliferative capacities, and cytokine producing capacities. For producing a cell preparation with a stable quality, it is necessary to prepare a purified and highly homogenous cell population. In addition, it has been pointed out that when a cell suspension comprising mesenchymal stem cells is intravenously administered, there is a risk that a cell aggregate consisting of the administered mesenchymal stem cells clogs a capillary vessel or a vessel thicker than that and thereby causes an embolus. Thus, from the viewpoint of improving the safety as a cell therapy agent, it is necessary to obtain mesenchymal stem cells having lower cell aggregability.

Patent Literature 1 discloses that cryopreserved amniotic mesenchymal cells can be produced as a cell preparation optimized for transplantation, by cryopreserving a mixture comprising amniotic mesenchymal cells in a particular cryopreservation solution to prevent a decrease in the survival rate of amniotic mesenchymal cells after thawing. However, this literature makes no mention about the selective preparation of mesenchymal stem cells having a particular excellent feature from among mesenchymal stem cells, specifically, the selective preparation of a cell population rich in mesenchymal stem cells having low cell aggregability, which is useful for intravenous administration of a cell preparation by utilizing the characteristics of mesenchymal stem cells as indices. Further, in Patent Literature 2, a mesenchymal stem cell population having high proliferative capacity and differentiation capacity is prepared by inoculating cells at a low density. However, this literature neither describes nor suggests a cell population rich in mesenchymal stem cells having low cell aggregability by utilizing characteristics of mesenchymal stem cells comprised in a mesenchymal stem cell population as indices.

Patent Literature 3 describes that mesenchymal stem cells secrete COL11A1 and COL16A1. However, Patent Literature 3 does not describe expression intensities of COL11A1 and COL16A1, and it neither describes nor suggests selectively preparing a cell population rich in mesenchymal stem cells having low cell aggregability by using characteristics of mesenchymal stem cells as indices.

An object of the present invention is to provide a cell population comprising mesenchymal cells having low cell aggregability, which are useful for intravenous administration of a cell preparation, and a method for producing the same, and a pharmaceutical composition comprising the cell population.

Solution to Problem

As a result of intensive studies in order to solve the above object, the present inventors have found that a cell population comprising cells collected from fetal appendages comprises mesenchymal stem cells having low expression levels of COL11A1 gene and COL16A1 gene, and further found that cell aggregation is reduced in a cell population comprising mesenchymal stem cells having the above cell characteristics. The present invention has been completed on the basis of these findings.

Specifically, the present specification provides the following invention.

[1] A method for producing a cell population comprising mesenchymal stem cells, the method comprising obtaining a cell population having the following cell characteristics: the cell population satisfies the relative expression level of COL11A1 gene to the expression level of SDHA gene of 6.0 or less and the relative expression level of COL16A1 gene to the expression level of SDHA gene of 1.5 or less.

[2] A cell population comprising mesenchymal stem cells, the cell population having the following cell characteristics:

the cell population satisfies the relative expression level of COL11A1 gene to the expression level of SDHA gene of 6.0 or less and the relative expression level of COL16A1 gene to the expression level of SDHA gene of 1.5 or less.

[3] The cell population according to [2], wherein the cell population satisfies the relative expression level of COL4A5 gene to the expression level of SDHA gene of 0.4 or less.

[4] The cell population according to [2] or [3], wherein the cell population satisfies any one or more of: the relative expression level of VCAN gene to the expression level of SDHA gene of 6.0 or less; the relative expression level of DCN gene to the expression level of SDHA gene of 3.0 or less; and the relative expression level of LUM gene to the expression level of SDHA gene of 6.0 or less.

[5] The cell population according to any one of [2] to [4], wherein the cell population satisfies the relative expression level of GPC4 gene to the expression level of SDHA gene of 0.5 or less.

[6] The cell population according to any one of [2] to [5], wherein the proportion of CDH6-positive mesenchymal stem cells is 30% or more in the cell population.

[7] The cell population according to any one of [2] to [6], wherein the mesenchymal stem cells are derived from a fetal appendage.

[8] A pharmaceutical composition comprising the cell population according to any one of [2] to [7], and a pharmaceutically acceptable vehicle.

[9] The pharmaceutical composition according to [8], wherein a single dose of mesenchymal stem cells to a human is $10^9$ cells/kg body weight or less.

[10] The pharmaceutical composition according to [8] or [9], wherein the pharmaceutical composition is a liquid preparation.

[11] The pharmaceutical composition according to any one of [8] to [10], wherein the pharmaceutical composition is an injectable liquid preparation.

[12] The pharmaceutical composition according to any one of [8] to [11], wherein the pharmaceutical composition is a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

[13] A cell population obtained by the production method according to [1].

[14] Use of the cell population according to any one of [2] to [7] for the manufacture of a pharmaceutical composition.

[15] Use according to [14], wherein the pharmaceutical composition is a pharmaceutical composition where a single dose of the mesenchymal stem cells to a human is $10^9$ cells/kg body weight or less.

[16] Use according to [14] or [15], wherein the pharmaceutical composition is a liquid preparation.

[17] Use according to any one of [14] to [16], wherein the pharmaceutical composition is an injectable liquid preparation.

[18] Use according to any one of [14] to [17], wherein the pharmaceutical composition is a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

[19] The cell population according to any one of [2] to [7] for use in the treatment of a disease.

[20] The cell population according to [19], wherein a single dose of the mesenchymal stem cells to a human is $10^9$ cells/kg body weight or less.

[21] The cell population according to [19] or [20], wherein the cell population is a liquid preparation.

[22] The cell population according to any one of [19] to [21], wherein the cell population is an injectable liquid preparation.

[23] The cell population according to any one of [19] to [22], wherein the disease is selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

[24] A method for treating a disease comprising administering the cell population according to any one of [2] to [7] to a patient in need of treatment.

[25] The method for treating a disease according to [24], wherein a single dose of the mesenchymal stem cells to a human is $10^9$ cells/kg body weight or less.

[26] The method for treating a disease according to [24] or [25], wherein the method is a liquid preparation.

[27] The method for treating a disease according to any one of [24] to [26], wherein the method is an injectable liquid preparation.

[28] The method for treating a disease according to any one of [24] to [27], wherein the disease is selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

[29] A composition comprising the cell population according to any one of [2] to [7] and a vehicle.

[30] A method for evaluating cell aggregability of mesenchymal stem cells in a cell population comprising the mesenchymal stem cells using the following cell characteristics as indices, the method comprising measuring the relative expression level of COL11A1 gene to the expression level of SDHA gene and the relative expression level of COL16A1 gene to the expression level of SDHA gene:
the cell population satisfies the relative expression level of COL11A1 gene to the expression level of SDHA gene of 6.0 or less and the relative expression level of COL16A1 gene to the expression level of SDHA gene of 1.5 or less.

[31] A method for evaluating a donor and/or a sample collected from the donor, comprising:
collecting a cell population comprising mesenchymal stem cells from the donor;
measuring the relative expression level of COL11A1 gene to the expression level of SDHA gene and the relative expression level of COL16A1 gene to the expression level of SDHA gene; and
evaluating the relative expression levels by using the following cell characteristics as indices:
the cell population satisfies the relative expression level of COL11A1 gene to the expression level of SDHA gene of 6.0 or less, and the relative expression level of COL16A1 gene to the expression level of SDHA gene of 1.5 or less.

[32] A method for determining and/or predicting an optimal condition for enzymatic treatment for a sample collected from a donor, the method comprising:
measuring the relative expression level of COL11A1 gene to the expression level of SDHA gene and the relative expression level of COL16A1 gene to the expression level of SDHA gene for a cell population obtained by enzymatically treating the sample; and
evaluating the relative expression levels by using the following cell characteristics as indices:
the cell population satisfies the relative expression level of COL11A1 gene to the expression level of SDHA gene of 6.0 or less and the relative expression level of COL16A1 gene to the expression level of SDHA gene of 1.5 or less.

Advantageous Effects of Invention

According to the present invention, a cell population comprising mesenchymal stem cells having low cell aggregability can be obtained. In addition, according to the present invention, relative expression levels of various genes to housekeeping genes can be used as indices for formation of a cell population comprising mesenchymal stem cells having low cell aggregability. This enables an efficient production of a cell preparation (pharmaceutical composition) useful for intravenous administration.

DESCRIPTION OF EMBODIMENTS

Figure 1:
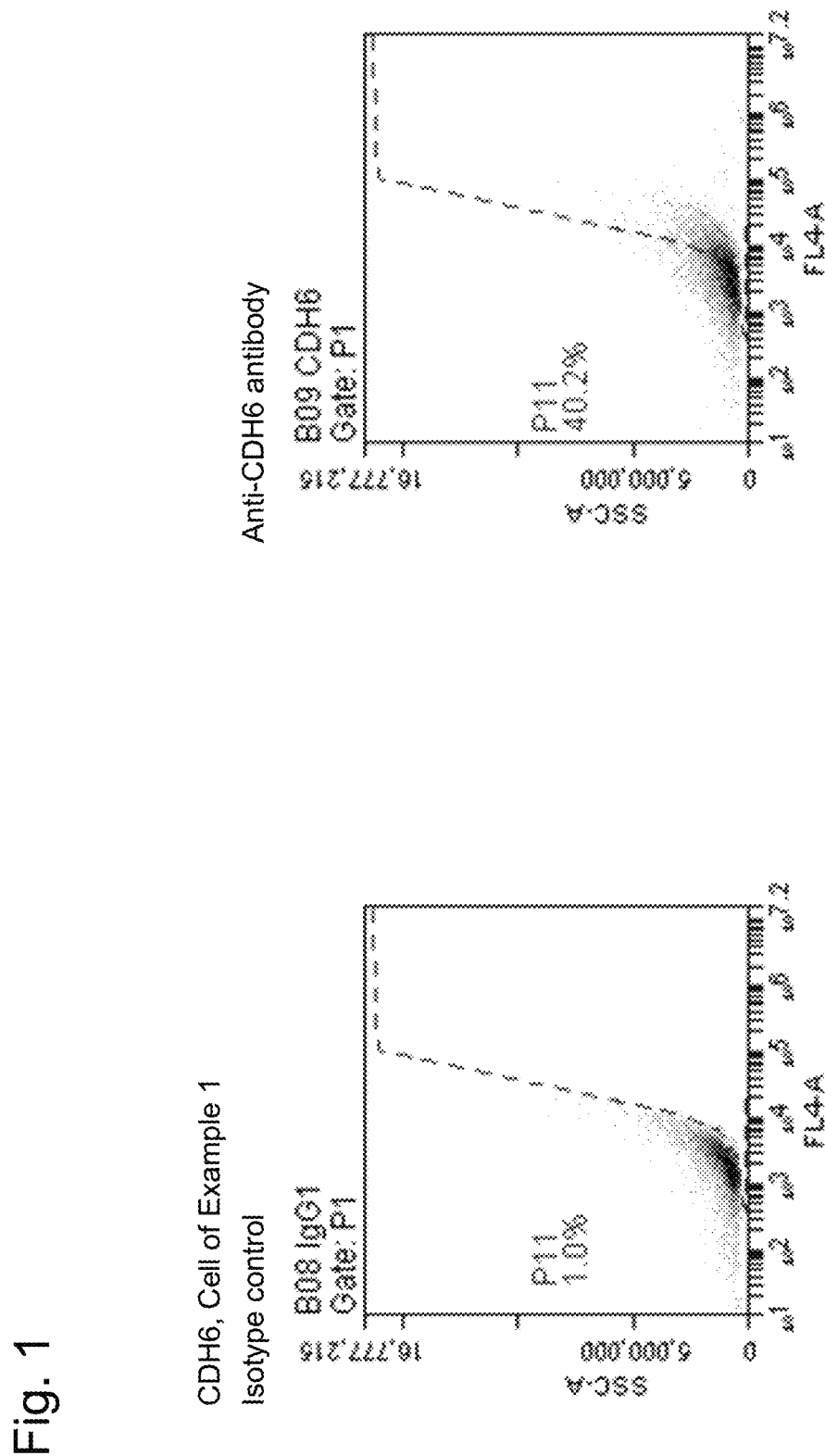
FIG. 1 shows results of measuring proportions of cells being positive for CDH6 by using a flow cytometer, for amniotic MSCs cultured in Example 1.

Embodiments of the present invention will be specifically described below. The descriptions below are intended to facilitate understanding of the present invention. Thus, the scope of the present invention is not limited to the following embodiments. Other embodiments, which a person skilled in the art may obtain as appropriate by replacing features of the following embodiments, are also included in the scope of the present invention.

[1] Explanation of Terms

The term "fetal appendage" used herein refers to a fetal membrane, a placenta, an umbilical cord, and amniotic fluid. In addition, the term "fetal membrane" refers to a fetal sac containing fetal amniotic fluid, which consists of an amnion, a chorion, and a decidua in that order from the inside. Among them, the amnion and the chorion are originated from the fetus. The term "amnion" refers to a transparent thin membrane with few blood vessels, which is located in the most inner layer of the fetal membrane. The inner layer (also called epithelial cell layer) of the amnion is covered with a layer of epithelial cells having a secretory function and secretes amniotic fluid. The outer layer (also called extracellular matrix layer, which corresponds to the stroma) of the amnion comprises mesenchymal stem cells.

The term "mesenchymal stem cells (MSCs)" used herein refers to stem cells that satisfy definitions described below, and are used interchangeably with "mesenchymal stromal cells." The term "mesenchymal stem cells" is also referred to as "MSCs" in the present specification.

Definition of Mesenchymal Stem Cells
i) Adherence to plastics under culture conditions in a standard medium.
ii) Positive for surface antigens CD105, CD73, and CD90, and negative for surface antigens CD45, CD34, CD11b, CD79alpha, CD19, and HLA-DR.

The term "mesenchymal stem cell population" used herein means a cell population comprising mesenchymal stem cells. Examples of the form thereof include, but are not particularly limited to, cell pellets, cell aggregates, cell-floated liquids and cell suspensions.

The term "amniotic mesenchymal stem cells" used herein refers to mesenchymal stem cells derived from the amnion, and are used interchangeably with "amniotic mesenchymal stromal cells." The term "amniotic mesenchymal stem cells" used herein is also referred to as "amniotic MSCs."

The term "cell aggregation" used herein means that a plurality of single cells are adhered to one another to form a group. Cell aggregation can be evaluated, for example, by observation using a microscope, or by cell counting using a cell counter, aggregation rate measurement, size distribution measurement or the like.

The phrase "proportion of CDH6-positive mesenchymal stem cells" used herein refers to the proportion of cells positive for the surface antigen analyzed by flow cytometry as described in Examples mentioned later. The phrase "proportion of CDH6-positive mesenchymal stem cells" used herein is also referred to as "positive rate."

[2] Cell Population Comprising Mesenchymal Stem Cells

The cell population comprising mesenchymal stem cells provided by the present invention is a cell population having the following cell characteristics:

the cell population satisfies the relative expression level of COL11A1 gene to the expression level of SDHA gene of 6.0 or less and the relative expression level of COL16A1 gene to the expression level of SDHA gene of 1.5 or less.

Satisfying the above conditions allows formation of a cell population comprising mesenchymal cells having low cell aggregability. Thus, in the present invention, the conditions can be used as indices for the formation of a cell population having low cell aggregability.

The upper limit of the relative expression level of COL11A1 gene to the expression level of SDHA gene may be 5.5 or less, 5.0 or less, 4.5 or less, 4.0 or less, 3.5 or less, 3.0 or less, 2.9 or less, 2.8 or less, 2.7 or less, 2.6 or less, 2.5 or less, 2.4 or less, 2.3 or less, 2.2 or less, 2.1 or less, 2.0 or less, 1.9 or less, 1.8 or less, 1.7 or less, 1.6 or less, 1.5 or less, 1.4 or less, 1.3 or less or 1.2 or less. Also, the lower limit of the relative expression level of COL11A1 gene to the expression level of SDHA gene may be 0.1 or more, 0.2 or more, 0.3 or more, 0.4 or more, 0.5 or more, 0.6 or more, 0.7 or more, 0.8 or more, 0.9 or more or 1.0 or more.

The upper limit of the relative expression level of COL16A1 gene to the expression level of SDHA gene may be 1.4 or less, 1.3 or less, 1.2 or less, 1.1 or less, 1.0 or less, 0.9 or less, 0.8 or less, 0.7 or less, 0.6 or less, 0.5 or less, 0.4 or less, 0.3 or less or 0.2 or less. Also, the lower limit of the relative expression level of COL16A1 gene to the expression level of SDHA gene may be 0.02 or more, 0.04 or more, 0.06 or more or 0.08 or more.

According to one aspect of the present invention, the cell population comprising mesenchymal stem cells provided by the present invention may satisfy the relative expression level of COL4A5 gene to the expression level of SDHA gene of 0.4 or less.

The upper limit of the relative expression level of COL4A5 gene to the expression level of SDHA gene may be 0.38 or less, 0.36 or less, 0.34 or less, 0.32 or less, 0.30 or less, 0.30 or less, 0.28 or less, 0.26 or less, 0.24 or less or 0.22 or less. Also, the lower limit of the relative expression level of COL4A5 gene to the expression level of SDHA gene may be 0.02 or more, 0.04 or more, 0.06 or more, 0.08 or more or 0.10 or more.

According to one aspect of the present invention, the cell population comprising mesenchymal stem cells provided by the present invention satisfies any one or more of: the relative expression level of VCAN gene to the expression level of SDHA gene of 6.0 or less; the relative expression level of DCN gene to the expression level of SDHA gene of 3.0 or less; and the relative expression level of LUM gene to the expression level of SDHA gene of 6.0 or less; preferably satisfies any two or more of the above; and more preferably satisfies all of the above.

The upper limit of the relative expression level of VCAN gene to the expression level of SDHA gene may be 5.5 or less, 5.0 or less, 4.5 or less, 4.0 or less, 3.9 or less, 3.8 or less, 3.7 or less or 3.6 or less. The lower limit of the relative expression level of VCAN gene to the expression level of SDHA gene may be 1.0 or more, 1.5 or more, 2.0 or more, 2.5 or more or 3.0 or more.

The upper limit of the relative expression level of DCN gene to the expression level of SDHA gene may be 2.9 or less, 2.8 or less, 2.7 or less, 2.6 or less, 2.5 or less, 2.4 or less, 2.3 or less, 2.2 or less, 2.1 or less, 2.0 or less or 1.9 or less. The lower limit of the relative expression level of DCN gene to the expression level of SDHA gene may be 1.0 or more, 1.1 or more, 1.2 or more, 1.3 or more, 1.4 or more, 1.5 or more, 1.6 or more or 1.7 or more.

The upper limit of the relative expression level of LUM gene to the expression level of SDHA gene may be 5.5 or less, 5.0 or less, 4.5 or less, 4.0 or less, 3.5 or less, 3.0 or less or 2.5 or less. The lower limit of the relative expression level of LUM gene to the expression level of SDHA gene may be 1.0 or more, 1.1 or more, 1.2 or more, 1.3 or more, 1.4 or more, 1.5 or more, 1.6 or more, 1.7 or more, 1.8 or more, 1.9 or more, 2.0 or more or 2.1 or more.

According to one aspect of the present invention, the cell population comprising mesenchymal stem cells provided by the present invention may satisfy the relative expression level of GPC4 gene to the expression level of SDHA gene of 0.5 or less.

The upper limit of the relative expression level of GPC4 gene to the expression level of SDHA gene may be 0.45 or less, 0.40 or less, 0.35 or less, 0.30 or less, 0.25 or less, 0.20 or less or 0.15 or less. In addition, the lower limit of the relative expression level of GPC4 gene to the expression level of SDHA gene may be 0.02 or more, 0.04 or more, 0.06 or more or 0.08 or more.

As a method for measuring the relative expression level of each gene to the expression level of SDHA gene, measurement using a microarray can be used. Microarray can be performed specifically by the following procedures (1) to (5). The following procedures (3) to (5) can be entrusted to and performed by RIKEN GENESIS Co., Ltd.

(1) If cells of interest are adherent cells, adherent cells are non-enzymatically dissociated from a plastic culture vessel using a cell scraper (manufactured by Corning Inc.), and are then collected by centrifugation. If cells of interest are non-adherent cells, they are collected by centrifugation.

(2) Using an RNA stabilization reagent (RNAlater (manufactured by Thermo Fisher Scientific Inc.)), the cells are stably preserved, and then, using an RNA extraction kit (RNeasy Plus Mini Kit (manufactured by QIAGEN)), total RNA is extracted and purified.

(3) Using the purified total RNA as a template, cDNA is synthesized by reverse transcription. Then, the synthesized cDNA is further transcribed to cRNA by in vitro transcription with biotin labeling.

(4) The biotin-labeled cRNA is added to a hybridization buffer and subjected to hybridization on Human GeneGenome U133A 2.0 Array (manufactured by Affymetrix, Inc.) for 16 hours, followed by washing with GeneChip Fluidics Station 450 (manufactured by Affymetrix, Inc.), staining with phycoerythrin, scanning using GeneChip Scanner 3000 7G (manufactured by Affymetrix, Inc.), image analysis using AGCC (Affymetrix GeneChip Command Console Software, manufactured by Affymetrix, Inc.), and then quantification using Affymetrix Expression Console (manufactured by Affymetrix, Inc.).

(5) Numerical data files are compared and analyzed using the analysis software GeneSpring GX (manufactured by Agilent Technologies, Inc.). For each cell, the relative expression level of each gene to the expression level of SDHA gene is calculated.

The sequence of SDHA (Succinate dehydrogenase complex, subunit A) gene is registered as ID: 6389 in the gene database of National Center for Biotechnology Information.

The sequence of VCAN (Versican) gene is registered as ID: 1462 in the gene database of National Center for Biotechnology Information.

The sequence of DCN (Decorin) gene is registered as ID: 1634 in the gene database of National Center for Biotechnology Information.

The sequence of LUM (Lumican) gene is registered as ID: 4060 in the gene database of National Center for Biotechnology Information.

The sequence of GPC4 (Glypican-4) gene is registered as ID: 2239 in the gene database of National Center for Biotechnology Information.

The sequence of COL11A1 (collagen type XI alpha 1 chain) gene is registered as ID: 1301 in the gene database of National Center for Biotechnology Information.

The sequence of COL16A1 (collagen type XVI alpha 1 chain) gene is registered as ID: 1307 in the gene database of National Center for Biotechnology Information.

The sequence of COL4A5 (Collagen Type IV Alpha 5 Chain) gene is registered as ID: 1287 in the gene database of National Center for Biotechnology Information.

The sequences of SDHA gene, VCAN gene, DCN gene, LUM gene, GPC4 gene, COL11A1 gene, COL16A1 gene and COL4A5 gene registered in the database as described above are herein incorporated by reference in their entirety.

The timing for measuring the gene expression level described above is not particularly limited, and examples thereof include immediately after separation of cells from a biological sample, during a culture step, after purification in the culture step, immediately after the Nth passage (N represents an integer of 1 or more), during maintenance culture, before cryopreservation, after thawing, before formulation, or after formulation.

According to one aspect of the present invention, the proportion of CDH6-positive mesenchymal stem cells in a cell population comprising mesenchymal stem cells provided by the present invention is 30% or more.

CDH6 refers to Cadherin6, and is one member of the cadherin superfamily. VCAN refers to Versican. DCN refers to Decorin. LUM refers tp Lumican.

The proportion of CDH6-positive mesenchymal stem cells in the cell population may be 31% or more, 32% or more, 33% or more, 34% or more, 35% or more, 36% or more, 37% or more, 38% or more, 39% or more, or 40% or more.

Each surface antigen marker can be detected by any detection method known in the art. Examples of the method for detecting a surface antigen marker include, but are not limited to, flow cytometry and cell staining. When cells that emit stronger fluorescence as compared with a negative control (isotype control) are detected in flow cytometry using a fluorescently labeled antibody, the cells are determined to be "positive" for the marker. Any antibody known in the art can be used as the fluorescently labeled antibody. Examples thereof include, but are not limited to, antibodies labeled with fluorescein isothiocyanate (FITC), phycoerythrin (PE), allophycocyanin (APC), or the like. When cells that are stained or emit fluorescence are observed under a microscope in cell staining, the cells are determined to be "positive" for the marker. The cell staining may be immunostaining of cells using an antibody, or may be non-immunostaining of cells without using an antibody.

The proportion of cells positive for each surface antigen marker (positive rate) can be measured specifically using a flow cytometry dot-plot analysis by the following procedures (1) to (8).

(1) When cells of interest are adherent cells, adherent cells are dissociated from a plastic culture vessel using trypsin-EDTA (Thermo Fisher Scientific Inc.), and are then collected by centrifugation. When cells of interest are non-adherent cells, they are collected by centrifugation.

(2) The cells are fixed with 4% paraformaldehyde and then washed with phosphate buffer (PBS), and a cell suspension is prepared in 2% BSA/PBS at $1.0 \times 10^6$ cells/mL. The cell suspension is dispensed in 100 µL each.

(3) The dispensed cell suspensions are centrifuged, and 100 µL of 0.5% BSA/PBS is each added to the obtained cell pellets, followed by addition of antibodies against the respective surface antigen markers or the isotype control antibodies thereof. For analyzing the surface antigen marker CDH6, Mouse IgG (H+L) is then added as a secondary antibody. Each reaction solution is mixed by vortexing and then allowed to stand at 4° C. for 20 minutes.

(4) The cells are washed by addition of 0.5% BSA/PBS and centrifugation, and then, the cells are suspended in 0.5% BSA/PBS and filtered through a cell strainer (35-m-nylon mesh filter) (Corning Inc./Product number: 352235).

(5) The cell suspension obtained by filtration is analyzed on a BD Accuri™ C6 Flow Cytometer (Becton, Dickinson and Company) with ALL Event 10000.

(6) The measurement results are plotted as dots with SSC (side scattered light) (numerical range: 0 or more and 16777215 or less) on the vertical axis and fluorescence intensity of the dye labeled to the antibody (numerical range: $10^1$ or more and $10^{7.2}$ or less) on the horizontal axis.

(7) In the dot plot diagram, all regions (gates) in which the cell population with stronger fluorescence intensity is 1.0% or less from all cells measured with the isotype control antibodies are selected.

(8) The proportion of cells contained in the gate selected in (7) among all cells measured with the antibody against the surface antigen marker is calculated.

The proportion of cells negative for each surface antigen (negative rate) is calculated by the following equation.

Negative rate (%)=100−Positive rate

The timing for detecting the surface antigen marker described above is not particularly limited, and examples thereof include immediately after separation of cells from a biological sample, during a culture step, after purification in the culture step, immediately after the Nth passage (N represents an integer of 1 or more), during maintenance culture, before cryopreservation, after thawing, before formulation, or after formulation.

The cell aggregability of a cell population can be evaluated by calculating a cell aggregability through the following procedures (1) to (6).

(1) A cell population is suspended in a medium (for example, αMEM (Alpha Modification of Minimum Essential Medium Eagle) containing 10% fetal bovine serum (FBS) (inactivated) and 1× Antibiotic-Antimycotic (manufactured by Thermo Fisher Scientific Inc.)) at a concentration of $2.0 \times 10^5$ cells/mL to be prepared as a cell suspension.

(2) 4 mL each of the prepared cell suspension is inoculated into a 6-well plate for suspension culture (Sumitomo Bakelite Co., Ltd./Product number: MS-8006R).

(3) The 6-well plate for suspension culture is placed on a shaker for use in an incubator, Orbital Shaker OS-762 (Optima Inc.) and is subjected to gyratory culture (suspension culture) for 24 hours in the environment of a $CO_2$ concentration of 3% or higher and 5% or lower and 37° C. under the condition of 90 rpm.

(4) The cell suspension obtained by gyratory culture is collected and filtered through a cell strainer (35-μm nylon mesh filter) (Corning Inc./Product number: 352235), and cell aggregates are trapped on a mesh.

(5) An unfiltered cell suspension (i.e., containing cell aggregates and single cells) and a cell suspension obtained by filtration (not containing cell aggregates) are stained with trypan blue, and cell counting is carried out using an automated cell counter, Countess II FL (Thermo Fisher Scientific Inc.).

(6) Cell aggregability is calculated by the following equation.

Cell aggregability (%)=100−(cell number per 1 mL of the cell suspension obtained by filtration/total number of cells per 1 mL of the unfiltered cell suspension)

The cell aggregability is preferably 65% or less, more preferably 60% or less, 55% or less, 50% or less, 45% or less, 40% or less, 35% or less, or 30% or less.

The timing for evaluating the cell aggregability described above is not particularly limited, and examples thereof include immediately after separation of cells from a biological sample, during a culture step, after purification in the culture step, immediately after the Nth passage (N represents an integer of 1 or more), during maintenance culture, before cryopreservation, after thawing, before formulation, or after formulation.

The cell population comprising mesenchymal stem cells provided by the present invention may be passaged. The lower limit of the number of passages is preferably 1 or more, more preferably 2 or more, further preferably 3 or more, further preferably 4 or more, and further preferably 5 or more. In addition, the upper limit of the number of passages is preferably 25 or less, further preferably 20 or less, further preferably 15 or less, and further preferably 10 or less.

Population doubling may be carried out on the cell population comprising mesenchymal stem cells provided by the present invention. The lower limit of the number of population doubling is preferably 5 or more, further preferably 10 or more, further preferably 15 or more, further preferably 20 or more, further preferably 25 or more, and further preferably 30 or more. In addition, the upper limit of the number of population doubling is preferably 60 or less, further preferably 55 or less, and further preferably 50 or less.

The number of population doubling is a number of times of division of cell population in a certain culture period and is calculated according to an equation: $[\log_{10}(\text{cell number at the completion of culture}) - \log_{10}(\text{cell number at the start of culture})]/\log_{10}(2)$. In a case where subculture is performed, the number of population doubling for each passage is calculated according to the equation described above and then cumulated, and thereby a total number of population doubling is calculated.

The origin of mesenchymal stem cells is not particularly limited, and mesenchymal stem cells derived from, for example, a fetal appendage, bone marrow, adipose or tooth pulp can be used. The mesenchymal stem cells are preferably mesenchymal stem cells derived from a fetal appendage, and more preferably mesenchymal stem cells derived from the amnion. The mesenchymal stem cells are mesenchymal stem cells isolated from an autologous, allogeneic or heterologous biological sample, and preferably mesenchymal stem cells isolated from an allogeneic biological sample.

The mesenchymal stem cells are recombinant or non-recombinant mesenchymal stem cells, and preferably non-recombinant mesenchymal stem cells.

The cell population of the present invention may contain any number of mesenchymal stem cells. The cell population of the present invention can include, but not limited to, not less or not more than $1.0 \times 10^1$, $1.0 \times 10^2$, $1.0 \times 10^3$, $1.0 \times 10^4$, $1.0 \times 10^5$, $1.0 \times 10^6$, $1.0 \times 10^7$, $1.0 \times 10^8$, $1.0 \times 10^9$, $1.0 \times 10^{10}$, $1.0 \times 10^{11}$, $1.0 \times 10^{12}$, or $1.0 \times 10^{13}$ mesenchymal stem cells.

The cell population of the present invention may comprise any component in addition to mesenchymal stem cells. Examples of such a component can include, but are not limited to, salts, polysaccharides (e.g., hydroxyethyl starch (HES) and dextran), proteins (e.g., albumin), DMSO, amino acids, and medium components (e.g., components contained in RPMI1640 medium).

The cell population of the present invention may be preserved in a frozen state until immediately before use. The cell population described above may comprise cryopreservation solution in addition to mesenchymal stem cells. As the cryopreservation solution described above, a commercially available cryopreservation solution may be used. Examples thereof include, but are not limited to, CP-1 (registered trademark) (manufactured by Kyokuto Pharmaceutical Industrial Co, Ltd.), BAMBANKER (manufactured by Lymphotec Inc.), STEM-CELLBANKER (manufactured by Nippon Zenyaku Kogyo Co., Ltd.), ReproCryo RM (manufactured by REPROCELL Inc.), CryoNovo (manufactured by Akron Biotechnology, LLC.), MSC Freezing Solution (manufactured by Biological Industries Inc.), and CryoStor (manufactured by HemaCare Inc.).

The cell population of the present invention may be provided as a composition in combination with a vehicle. As the vehicle, preferably a liquid vehicle (e.g., media, DMSO, cryopreservation solutions or pharmaceutically acceptable vehicles described below) can be used.

The composition comprising the cell population of the present invention and the vehicle may be in any cell concentration. Exemplary cell concentrations of the composition comprising the cell population of the present invention and a vehicle include, but are not limited to, not less or not more than $1.0\times10^1$ cells/mL, $1.0\times10^2$ cells/mL, $1.0\times10^3$ cells/mL, $1.0\times10^4$ cells/mL, $1.0\times10^5$ cells/mL, $1.0\times10^6$ cells/mL, $1.0\times10^7$ cells/mL, $1.0\times10^8$ cells/mL, $1.0\times10^9$ cells/mL, or $1.0\times10^{10}$ cells/mL.

[3] Method for Producing a Cell Population Comprising Mesenchymal Stem Cells

The method for producing a cell population comprising mesenchymal stem cells according to the present invention is a method comprising obtaining a cell population having the following cell characteristics:
the cell population satisfies the relative expression level of COL11A1 gene to the expression level of SDHA gene of 6.0 or less and the relative expression level of COL16A1 gene to the expression level of SDHA gene of 1.5 or less.

In other words, the method for producing a cell population comprising mesenchymal stem cells according to the present invention is a method comprising a step of preparing a cell population comprising mesenchymal stem cells under such a condition that the cell characteristics described above (the condition that the cell population comprising mesenchymal stem cells satisfies the relative expression level of COL11A1 gene to the expression level of SDHA gene of 6.0 or less and the relative expression level of COL16A1 gene to the expression level of SDHA gene of 1.5 or less) are maintained. The condition described above serves as indices for formation of a cell population comprising mesenchymal stem cells having low cell aggregability; and the production method of the present invention is not particularly limited as long as the indices are satisfied.

The production method of the present invention may comprise a cell population obtainment step of obtaining a cell population comprising mesenchymal stem cells by enzymatically treating a sample (for example, a fetal appendage such as the amnion) comprising mesenchymal stem cells. The cell population obtainment step may be a step comprising a step of obtaining the amnion by cesarean section. In addition, the cell population obtainment step may comprise a step of washing a sample comprising mesenchymal stem cells.

The amnion consists of an epithelial cell layer and an extracellular matrix layer, and the latter layer comprises amniotic mesenchymal stem cells. Like other epithelial cells, the amniotic epithelial cells are characterized by expression of epithelial cadherin (E-cadherin: CD324) and an epithelial adhesion factor (EpCAM: CD326). On the other hand, the amniotic MSCs do not express such epithelial-specific surface antigen markers and they can be easily distinguished by flow cytometry.

The cell population comprising mesenchymal stem cells according to the present invention is preferably a cell population obtained by treating a sample comprising an epithelial cell layer and an extracellular matrix layer collected from a fetal appendage with at least collagenase.

The enzymatic treatment of the sample collected from a fetal appendage (preferably a sample comprising an epithelial cell layer and an extracellular matrix layer) is preferably a treatment with an enzyme (or a combination of enzymes) that can release mesenchymal stem cells contained in the extracellular matrix layer of the fetal appendage, and does not degrade the epithelial cell layer. Examples of such an enzyme can include, but are not particularly limited to, collagenase and/or metalloproteinase. Examples of the metalloproteinase can include, but are not particularly limited to, thermolysin and/or dispase, which is metalloproteinase that cleaves nonpolar amino acids at their N-terminal sides.

The active concentration of the collagenase is preferably 50 PU/ml or higher, more preferably 100 PU/ml or higher, further preferably 200 PU/ml or higher, further preferably 300 PU/ml or higher, and further preferably 400 PU/ml or higher. The active concentration of the collagenase is, but is not particularly limited to, for example, 1000 PU/ml or lower, 900 PU/ml or lower, 800 PU/ml or lower, 700 PU/ml or lower, 600 PU/ml or lower, or 500 PU/ml or lower. In this context, PU (Protease Unit) is defined as the amount of the enzyme that degrades 1 μg of FITC-collagen in 1 minute at 30° C. and pH 7.5.

The active concentration of the metalloproteinase (e.g., thermolysin and/or dispase) is preferably 50 PU/ml or higher, more preferably 100 PU/ml or higher, further preferably 200 PU/ml or higher, further preferably 300 PU/ml or higher, and further preferably 400 PU/ml or higher. Also, the active concentration of the metalloproteinase is preferably 1000 PU/ml or lower, more preferably 900 PU/ml or lower, further preferably 800 PU/ml or lower, further preferably 700 PU/ml or lower, further preferably 600 PU/ml or lower, and further preferably 500 PU/ml or lower. In this context, PU (Protease Unit) in an aspect of using dispase as the metalloproteinase is defined as the amount of the enzyme that releases an amino acid corresponding to 1 μg tyrosine from casein lactate in 1 minute at 30° C. and pH 7.5. In the concentration range of the enzyme described above, mesenchymal stem cells contained in the extracellular matrix layer can be efficiently released while preventing contamination with epithelial cells contained in the epithelial cell layer of the fetal appendage. The preferred combination of the concentrations of the collagenase and/or the metalloproteinase can be determined by the microscopic observation of the fetal appendage after the enzymatic treatment, or the flow cytometry of the obtained cells.

It is preferred to treat the fetal appendage at the same time with collagenase and metalloproteinase in combination, from the viewpoint of efficiently collecting live cells. In this case, thermolysin and/or dispase can be used as the metalloproteinase, though the metalloproteinase is not limited thereto. Mesenchymal stem cells can be easily obtained by treating the fetal appendage only once with an enzyme solution containing collagenase and metalloproteinase. The treatment at the same time can reduce the risk of contamination by bacteria, viruses, and the like.

For the enzymatic treatment of the fetal appendage, it is preferred to immerse the amnion washed using a washing solution such as physiological saline or Hank's balanced salt solution in the enzyme solution, and perform the treatment with stirring using stirring means. A stirrer or a shaker can be used as such stirring means from the viewpoint of efficiently releasing mesenchymal stem cells contained in the extracellular matrix layer of the fetal appendage, though the stirring means is not limited thereto. The stirring rate is not particularly limited and is, for example, 5 rpm or more, 10 rpm or more, 20 rpm or more, 30 rpm or more, 40 rpm or more or 50 rpm or more when using a stirrer or a shaker. Also, the stirring rate is not particularly limited and is, for example, 100 rpm or less, 90 rpm or less, 80 rpm or less, 70 rpm or less or 60 rpm or less when using a stirrer or a shaker. The enzymatic treatment duration is not particularly limited and is, for example, 10 minutes or longer, 20 minutes or longer, 30 minutes or longer, 40 minutes or longer, 50 minutes or longer, 60 minutes or longer, 70 minutes or longer, 80 minutes or longer or 90 minutes or longer. Also, the enzymatic treatment duration is not particularly limited and is, for example, 6 hours or shorter, 5 hours or shorter, 4 hours or shorter, 3 hours or shorter, 2 hours or shorter, 110 minutes or shorter, 100 minutes or shorter. The enzymatic treatment temperature is not particularly limited and is, for example, 15° C. or higher, 16° C. or higher, 17° C. or higher, 18° C. or higher, 19° C. or higher, 20° C. or higher, 21° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, 35° C. or higher or 36° C. or higher. Also, the enzymatic treatment temperature is not particularly limited and is, for example, 40° C. or lower, 39° C. or lower, 38° C. or lower or 37° C. or lower.

In the production method of the present invention, if desired, the released mesenchymal stem cells can be separated and/or collected from the enzyme solution containing the released mesenchymal stem cells by a known method such as a filter, centrifugation, a hollow fiber separation membrane, or a cell sorter. Preferably, the enzyme solution containing the released mesenchymal stem cells is filtered through a filter. In an aspect of filtering the enzyme solution through a filter, only the released cells pass through the filter, whereas an undegraded epithelial cell layer remains on the filter without passing through the filter. Therefore, not only can the released mesenchymal stem cells be easily separated and/or collected, but the risk of contamination by bacteria, viruses, and the like can be reduced. Examples of the filter can include, but are not particularly limited to, mesh filters. The pore size (mesh size) of the mesh filter is not particularly limited and is, for example, 40 μm or larger, 50 μm or larger, 60 μm or larger, 70 μm or larger, 80 μm or larger, or 90 μm or larger. Also, the pore size of the mesh filter is not particularly limited and is, for example, 200 μm or smaller, 190 μm or smaller, 180 μm or smaller, 170 μm or smaller, 160 μm or smaller, 150 μm or smaller, 140 μm or smaller, 130 μm or smaller, 120 μm or smaller, 110 μm or smaller, or 100 μm or smaller. The filtration rate is not particularly limited. By using the pore size of the mesh filter within the range described above, the enzyme solution containing the mesenchymal stem cells can be filtered by free fall. This can prevent decrease in cell survival rate.

Nylon is preferably used as a material for the mesh filter. A tube containing a 40 μm, 70 μm, 95 μm or 100 μm nylon mesh filter such as a Falcon cell strainer, which is widely used for research purposes, can be used. Alternatively, medical mesh cloth (nylon and polyester) used for hemodialysis and the like can be used. Further, an arterial filter used for extracorporeal circulation (polyester mesh filter, pore size: 40 μm or larger and 120 μm or smaller) can also be used. A mesh made of any other material, for example, a stainless-steel mesh filter, may also be used.

Preferably, the mesenchymal stem cells are allowed to pass through a filter in natural drop (free fall). It is also possible to force the cells to pass through a filter by suction using a pump or the like. In this case, minimum necessary pressurization is desirable in order to avoid damage of the cells.

The mesenchymal stem cells that have passed through the filter can be collected by centrifugation after dilution of the filtrate with two times or more its volume of a medium or balanced salt buffer solution. Examples of the balanced salt buffer solution that can be used include, but are not limited to, Dulbecco's phosphate buffer (DPBS), Earle's balanced salt solution (EBSS), Hank's balanced salt solution (HBSS), and phosphate buffer (PBS).

The cell population obtained by the cell population obtainment step described above is prepared under the following conditions: the cell population satisfies the relative expression level of COL11A1 gene to the expression level of SDHA gene of 6.0 or less and the relative expression level of COL16A1 gene to the expression level of SDHA gene of 1.5 or less. The condition is useful as indices for obtaining a cell population comprising mesenchymal stem cells having low cell aggregability. The preparation method is not particularly limited as long as the indices are satisfied. Examples of such a method may include: separating a cell population satisfying the relative expression level of COL11A1 gene to the expression level of SDHA gene of 6.0 or less by a cell sorter, and then, selecting from the obtained cell population a cell population satisfying the relative expression level of COL16A1 gene to the expression level of SDHA gene of 1.5 or less; selecting a cell population satisfying the relative expression level of COL16A1 gene to the expression level of SDHA gene of 1.5 or less, and then separating from the obtained cell population a cell population satisfying the relative expression level of COL11A1 gene to the expression level of SDHA gene of 6.0 or less by a cell sorter. In addition, another method for preparing a cell population satisfying the indices may be to culture a cell population under a condition satisfying the two conditions described above (the cell population satisfies the relative expression level of COL11A1 gene to the expression level of SDHA gene of 6.0 or less and the relative expression level of COL16A1 gene to the expression level of SDHA gene of 1.5 or less).

Examples of a culture method satisfying the indices include a step of repeating a plurality of times the inoculation of the cell population into an uncoated plastic culture vessel at a density of 400 to 5,000 cells/cm$^2$ followed by culture. The density of the cell population for inoculation is further preferably 500 cells/cm$^2$ or more, further preferably 600 cells/cm$^2$ or more, further preferably 700 cells/cm$^2$ or more, further preferably 800 cells/cm$^2$ or more, further preferably 900 cells/cm$^2$ or more, further preferably 1000 cells/cm$^2$ or more, further preferably 1100 cells/cm$^2$ or more, further preferably 1200 cells/cm$^2$ or more, further preferably 1300 cells/cm$^2$ or more, further preferably 1400 cells/cm$^2$ or more, further preferably 1500 cells/cm$^2$ or more, further preferably 1600 cells/cm$^2$ or more, further preferably 1700 cells/cm$^2$ or more, further preferably 1800 cells/cm$^2$ or more, further preferably 1900 cells/cm$^2$ or more, and further preferably 2000 cells/cm$^2$ or more. The density of the cell population for inoculation is further preferably 4800 cells/cm$^2$ or less, further preferably 4600 cells/cm$^2$ or less, further preferably 4400 cells/cm$^2$ or less, further preferably 4200 cells/cm$^2$ or less, further preferably 4000 cells/cm$^2$ or less, further preferably 3800 cells/cm$^2$ or less, further preferably 3600 cells/cm$^2$ or less, further preferably 3400 cells/cm$^2$ or less, further preferably 3200 cells/cm$^2$ or less, further preferably 3000 cells/cm$^2$ or less, further preferably 2800 cells/cm$^2$ or less, further preferably 2600 cells/cm$^2$ or less, further preferably 2400 cells/cm$^2$ or less, and further preferably 2200 cells/cm$^2$ or less.

Examples of the other culture methods that satisfy the indices include a step of repeating a plurality of times the inoculation of the cell population into a plastic culture vessel coated with a coating agent at a density of 400 to 5,000 cells/cm$^2$ followed by culture. Preferred density conditions for the inoculation of the cell population are similar to the conditions described above.

Examples of the coating agent include, but are not limited to, extracellular matrix, fibronectin, vitronectin, osteopontin, laminin, entactin, collagen I, collagen II, collagen III, collagen IV, collagen V, collagen VI, gelatin, poly-L-ornithine, poly-D-lysine, and Matrigel (registered trademark) matrix.

Examples of further other culture methods that satisfy the indices include culturing with addition of basic fibroblast growth factor (bFGF) to the basal medium for use in the culture. The concentration of the basic fibroblast growth factor is preferably 2 ng/mL or more, further preferably 4 ng/mL or more, further preferably 6 ng/mL or more, further preferably 8 ng/mL or more, and further preferably 10 ng/mL or more. The concentration of the basic fibroblast growth factor is preferably 20 ng/mL or less, further preferably 18 ng/mL or less, 16 ng/mL or less, further preferably 14 ng/mL or less, and further preferably 12 ng/mL or less. The timing for adding the basic fibroblast growth factor is not particularly limited, and examples thereof include the beginning of a culture step, during the culture step, after purification in the culture step, immediately after the Nth passage (N represents an integer of 1 or more), during maintenance culture, before cryopreservation, or after thawing.

Examples of the culture period of one culture process can include 4 to 10 days and can more specifically include 4 days, 5 days, 6 days, 7 days, 8 days, 9 days and 10 days.

The medium for use in the culture can be prepared by utilizing any liquid medium for animal cell culture as a basal medium and, if necessary, appropriately adding other components (serum, a serum replacement reagent, a growth factor, etc.) thereto.

Examples of the basal medium that can be used include, but are not particularly limited to, media such as BME medium, BGJb medium, CMRL1066 medium, Glasgow MEM medium, improved MEM zinc option medium, IMDM medium (Iscove's modified Dulbecco's medium), Medium 199 medium, Eagle MEM medium, aMEM (alpha modification of minimum essential medium eagle) medium, DMEM medium (Dulbecco's modified Eagle's medium), Ham's F10 medium, Ham's F12 medium, RPMI 1640 medium, Fischer's medium, and mixed medium thereof (e.g., DMEM/F12 medium (Dulbecco's modified Eagle's medium/nutrient mixture F-12 Ham)).

Alternatively, the medium for use in the culture may be a commercially available serum-free medium. Examples thereof include, but are not particularly limited to, STK1 and STK2 (DS Pharma Biomedical Co., Ltd.), EXPREP MSC Medium (BioMimetics Sympathies Inc.), and Corning stemgro human mesenchymal stem cell medium (Corning Inc.).

Examples of other components to be added to the basal medium include albumin, serum, serum replacement reagents and growth factors. In an aspect of adding albumin to the basal medium, the concentration of albumin is preferably higher than 0.05% and 5% or lower. In an aspect of adding serum to the basal medium, the concentration of serum is preferably 5% or higher. In an aspect of adding a growth factor, a reagent (heparin, etc.) for stabilizing the growth factor in the medium may be further added in addition to the growth factor; or the growth factor may be stabilized with a gel, a polysaccharide or the like in advance, and then adding the stabilized growth factor to the basal medium.

The culture of mesenchymal stem cells can be performed by, for example, the following process. First, a cell suspension is centrifuged, the supernatant is removed, and the obtained cell pellet is suspended in a medium. Next, the cells are inoculated into an uncoated plastic culture vessel and cultured to 95% or less confluence using a medium in an environment of a $CO_2$ concentration of 3% or higher and 5% or lower at 37° C. Examples of the medium can include, but are not limited to, aMEM, M199, and media based thereon. The cells obtained by the culture as described above are cells cultured once.

The cells cultured once described above can be further passaged and cultured, for example, as follows: first, the cells cultured once are treated by cell dissociation means, then treated with trypsin, and thereby dissociated from the plastic culture vessel. Next, the obtained cell suspension is centrifuged, the supernatant is removed, and the obtained cell pellet is suspended in a medium. Finally, the cells are inoculated to an uncoated plastic culture vessel, and cultured to 95% or less confluence using a medium in an environment of a $CO_2$ concentration of 3% or higher and 5% or lower at 37° C. Examples of the medium can include, but are not limited to, αMEM, M199, and media based thereon. The cells obtained by the passage and the culture as described above are cells passaged once. Cells passaged N times can be obtained by similar passage and culture (N represents an integer of 1 or more). From the viewpoint of producing the cells at a large scale, the lower limit of passage number N is, for example, 1 or more, preferably 2 or more, more preferably 3 or more, further preferably 4 or more, further preferably 5 or more, further preferably 6 or more, further preferably 7 or more, further preferably 8 or more, further preferably 9 or more, further preferably 10 or more, further preferably 11 or more, further preferably 12 or more, further preferably 13 or more, further preferably 14 or more, further preferably 15 or more, further preferably 16 or more, further preferably 17 or more, further preferably 18 or more, further preferably 19 or more, further preferably 20 or more, and further preferably 25 or more. In addition, from the viewpoint of suppressing cell senescence, the upper limit of passage number N is, for example, preferably 50 or less, 45 or less, 40 or less, 35 or less, or 30 or less.

As the cell dissociation means, a cell dissociation agent, for example, may be used. As the cell dissociation agent, trypsin, collagenase, dispase, ethylenediaminetetraacetic acid (EDTA) or the like can be used, but the cell dissociation agent is not particularly limited. As the cell dissociation agent, a commercially available cell dissociation agent may be used. Examples thereof include, but are not limited to, trypsin-EDTA solution (manufactured by Thermo Fisher Scientific Inc.), TrypLE Select (manufactured by Thremo Fisher Scientific Inc.), Accutase (manufactured by Stemcell Technologies Inc.), and Accumax (manufactured by Stemcell Technologies Inc.). In addition, as cell dissociation means, physical cell dissociation means may be used, and examples thereof to be used include, but are not limited to, a cell scraper (manufacture by Corning Inc.). Cell dissociation means may be used alone or a plurality of cell dissociation means may be used in combination.

According to the production method of the present invention, a cell population comprising mesenchymal stem cells having low cell aggregability can be obtained, and this enables production of a cell preparation (pharmaceutical composition) useful for intravenous administration. The lower limit of the obtained cell number per batch of culture (cell number obtained per unit surface area and per unit number of culture days) differs depending on an inoculated cell number, an inoculation density, etc. and is, for example, $1.0\times10^5$ (cells/cm$^2$/day) or more, $2.0\times10^5$ (cells/cm$^2$/day) or more, $3.0\times10^5$ (cells/cm$^2$/day) or more, $4.0\times10^5$ (cells/cm$^2$/day) or more, $5.0\times10^5$ (cells/cm$^2$/day) or more, $6.0\times10^5$ (cells/cm$^2$/day) or more, $7.0\times10^5$ (cells/cm$^2$/day) or more, $8.0\times10^5$ (cells/cm$^2$/day) or more, $9.0\times10^5$ (cells/cm$^2$/day) or more or $10.0\times10^5$ (cells/cm$^2$/day) or more. Also, the upper limit of the obtained cell number per batch of culture is not particularly limited and is, for example, $10.0 \times 10^8$ (cells/cm$^2$/day) or less, $9.0 \times 10^8$ (cells/cm$^2$/day) or less, $8.0 \times 10^8$ (cells/cm$^2$/day) or less, $7.0 \times 10^8$ (cells/cm$^2$/day) or less, $6.0 \times 10^8$ (cells/cm$^2$/day) or less, $5.0 \times 10^8$ (cells/cm$^2$/day) or less, $4.0 \times 10^8$ (cells/cm$^2$/day) or less, $3.0 \times 10^8$ (cells/cm$^2$/day) or less, $2.0 \times 10^8$ (cells/cm$^2$/day) or less or $1.0 \times 10^8$ (cells/cm$^2$/day) or less.

According to the production method of the present invention, a cell population comprising mesenchymal stem cells having low cell aggregability can be obtained. The mesenchymal stem cells obtained by the production method of the present invention can be cultured preferably up to 40 days or later, more preferably up to 45 days or later, up to 50 days or later, up to 55 days or later, up to 60 days or later, up to 65 days or later, up to 70 days or later, up to 75 days or later, up to 80 days or later, up to 85 days or later, up to 90 days or later, up to 95 days or later, up to 100 days or later, up to 105 days or later, or up to 110 days or later, after the start of in vitro culture.

The mesenchymal stem cells obtained by the production method of the present invention can also be cultured up to doubling number of preferably 10 or more, more preferably 15 or more, 20 or more, 25 or more, 30 or more, 35 or more, 40 or more, 45 or more, or 50 or more, after the start of in vitro culture.

The production method of the present invention may comprise an identification step of identifying a cell population comprising mesenchymal stem cells having low cell aggregability by using, as indices, a condition that the cell population satisfies the relative expression level of COL11A1 gene to the expression level of SDHA gene of 6.0 or less and the relative expression level of COL16A1 gene to the expression level of SDHA gene of 1.5 or less.

Means for identifying the cell population comprising mesenchymal stem cells is preferably flow cytometry, microarray and/or quantitative RT-PCR.

The relative expression levels of COL11A1 gene and COL16A1 gene to the expression level of SDHA gene can be measured using microarray in accordance with the procedures described above in the present specification.

The timing to perform the above identification is not particularly limited, and examples thereof include immediately after separation of cells from a biological sample, during a culture step, after purification in the culture step, immediately after the Nth passage (N represents an integer of 1 or more), during maintenance culture, before cryopreservation, after thawing, before formulation, or after formulation.

In addition, the production method of the present invention may include a step of selectively separating the identified cell population after identifying the cell population comprising the mesenchymal stem cells by using the above conditions as indices. Means for selectively separating the identified cell population is not particularly limited, but examples thereof include separation of a cell population by a cell sorter, and purification of a cell population by culture.

The production method of the present invention may also comprise a step of cryopreserving the cell population comprising mesenchymal stem cells. In an aspect comprising the step of cryopreserving the cell population, the cell population may be thawed, and then, if necessary, identified, separated, collected and/or cultured. Alternatively, the cell population may be thawed and then directly used.

Examples of the means for cryopreserving the cell population comprising mesenchymal stem cells include, but are not particularly limited to, program freezers, deep freezers, and immersing in liquid nitrogen. In the case of using a program freezer, the temperature for freezing is preferably −30° C. or lower, −40° C. or lower, −50° C. or lower, −60° C. or lower, −70° C. or lower, −80° C. or lower, −90° C. or lower, −100° C. or lower, −110° C. or lower, −120° C. or lower, −130° C. or lower, −140° C. or lower, −150° C. or lower, −160° C. or lower, −170° C. or lower, −180° C. or lower, −190° C. or lower, or −196° C. (liquid nitrogen temperature) or lower. In the case of using a program freezer, the freezing rate for freezing is, for example, preferably −1° C./min, −2° C./min, −3° C./min, −4° C./min, −5° C./min, −6° C./min, −7° C./min, −8° C./min, −9° C./min, −10° C./min, −11° C./min, −12° C./min, −13° C./min, −14° C./min or −15° C./min. In the case of using a program freezer as such freezing means, the temperature can be lowered to a temperature between −50° C. or higher and −30° C. or lower (e.g., −40° C.) at a freezing rate of, for example, −2° C./min or more and −1° C./min or less, and further lowered to a temperature of −100° C. or higher and −80° C. or lower (e.g., −90° C.) at a freezing rate of −11° C./min or more and −9° C./min or less (e.g., −10° C./min). In addition, when immersing in liquid nitrogen is used as such freezing means, the temperature can be rapidly lowered to, for example −196° C. for freezing, and then, cryopreservation can be carried out in liquid nitrogen (gas phase).

For freezing by the freezing means, the cell population may be frozen in a state contained in any preservation container. Examples of such a preservation container include, but are not limited to, cryotubes, cryovials, freezing bags, and infusion bags.

For freezing by the freezing means, the cell population may be frozen in any cryopreservation solution. Examples of such a cryopreservation solution include, but are not limited to, BAMBANKER (manufactured by Lymphotec Inc.), STEM-CELLBANKER (manufactured by Nippon Zenyaku Kogyo Co., Ltd.), ReproCryo RM (manufactured by REPROCELL Inc.), CryoNovo (Akron Biotechnology, LLC.), MSC Freezing Solution (Biological Industries Inc.), and CryoStor (HemaCare Inc.).

The cryopreservation solution can contain polysaccharides at a defined concentration. The preferable concentration of polysaccharides is, for example, 1% by mass or higher, 2% by mass or higher, 3% by mass or higher, 4% by mass or higher, 5% by mass or higher, 6% by mass or higher, 7% by mass or higher, 8% by mass or higher, 9% by mass or higher, 10% by mass or higher, 11% by mass or higher or 12% by mass or higher. In addition, the preferable concentration of polysaccharides is, for example, 40% by mass or lower, 35% by mass or lower, 30% by mass or lower, 25% by mass or lower, 20% by mass or lower, 19% by mass or lower, 18% by mass or lower, 17% by mass or lower, 16% by mass or lower, 15% by mass or lower, 14% by mass or lower or 13% by mass or lower. Examples of the polysaccharide include, but are not limited to, hydroxyethyl starch (HES) and dextran (Dextran40 or the like).

The cryopreservation solution can contain dimethyl sulphoxide (DMSO) at a defined concentration. The preferable concentration of DMSO is, for example, 1% by mass or higher, 2% by mass or higher, 3% by mass or higher, 4% by mass or higher, 5% by mass or higher, 6% by mass or higher, 7% by mass or higher, 8% by mass or higher or 9% by mass or higher. In addition, the preferable concentration of DMSO is, for example, 20% by mass or lower, 19% by mass or lower, 18% by mass or lower, 17% by mass or lower, 16% by mass or lower, 15% by mass or lower, 14% by mass or lower, 13% by mass or lower, 12% by mass or lower, 11% by mass or lower or 10% by mass or lower.

The cryopreservation solution may be a solution containing albumin at a defined concentration higher than 0% by mass. The preferable concentration of albumin is, for example, 0.5% by mass or higher, 1% by mass or higher, 2% by mass or higher, 3% by mass or higher, 4% by mass or higher, 5% by mass or higher, 6% by mass or higher, 7% by mass or higher or 8% by mass or higher. In addition, the preferable concentration of albumin is, for example, 40% by mass or lower, 35% by mass or lower, 30% by mass or lower, 25% by mass or lower, 20% by mass or lower, 15% by mass or lower, 10% by mass or lower or 9% by mass or lower. Examples of albumin can include, but are not limited to, bovine serum albumin, mouse albumin, and human albumin.

The production method of the present invention can comprise a step of washing the cell population comprising mesenchymal stem cells. Examples of a washing solution to be used in the step of washing the cell population comprising mesenchymal stem cells include, but are not limited to, physiological saline, Dulbecco's phosphate buffer (DPBS), Earle's balanced salt solution (EBSS), Hank's balanced salt solution (HBSS) and phosphate-buffer (PBS). Washing a cell population can reduce or remove allergen, endotoxin or the like. Examples of the allergen include, but are not limited to, bovine serum albumin (BSA), swine trypsin and swine heparin.

The production method of the present invention can comprise a step of filling the cell population comprising mesenchymal stem cells into a preservation container. Examples of such a preservation container include, but are not limited to, cryotubes, cryovials, freezing bags, and infusion bags.

[4] Method for Evaluating Cell Aggregability of Mesenchymal Stem Cells, Method for Evaluating Donor and/or Sample Collected from the Donor, and Method for Determining and/or Predicting an Optimal Enzymatic Treatment Condition In the present invention, in a cell population comprising mesenchymal stem cells, the cell aggregability of mesenchymal stem cells can be evaluated by performing measurement (preferably by performing measurement over time) utilizing, as indices, a condition that the cell population satisfies the relative expression level of COL11A1 gene to the expression level of SDHA gene of 6.0 or less and the relative expression level of COL16A1 gene to the expression level of SDHA gene of 1.5 or less. Examples of the step that requires the evaluation include a culture step, a cryopreservation step and/or a formulation step.

In the culture step, for example, measurement of the indices over time allows changes in the cell aggregability of mesenchymal stem cells to be quickly and easily known and predicted. It can be known that in a cell population comprising mesenchymal stem cells satisfying the indices, the mesenchymal stem cells maintain low aggregability. On the other hand, when a culture state continues with a value deviating from the indices, it can be predicted that the cell aggregability of the mesenchymal stem cells is increasing. When it is found from the indices that the cell aggregability is increasing, the cell aggregation can be reduced by properly changing culture conditions (change of an inoculation density, a medium, a growth factor, serum, etc.) as needed. In addition, when the indices are not satisfied, only a cell population comprising mesenchymal stem cells that satisfy the indices can be separated through the use of, for example, a cell sorting technique. Thereafter, mesenchymal stem cells in the cell population are inoculated again and subcultured, and thereby the cell aggregation can be reduced. At the early stage of culture, culture conditions (change of an inoculation density, a medium, a growth factor, serum, etc.) may be designed such that the indices are satisfied at the final stage of the step, and thus, the indices may be satisfied at least at the final stage.

In the present invention, the quality of a donor itself and/or a sample collected from the donor can be evaluated by obtaining a cell population comprising mesenchymal stem cells from the donor, measuring the relative expression level of COL11A1 gene to the expression level of SDHA gene and the relative expression level of COL16A1 gene to the expression level of SDHA gene, performing the measurement using as indices a condition that the cell population satisfies the relative expression level of COL11A1 gene to the expression level of SDHA gene of 6.0 or less and the relative expression level of COL16A1 gene to the expression level of SDHA gene of 1.5 or less. When a cell population comprising mesenchymal stem cells that satisfy the indices is obtained (preferably, easily obtained), the quality of the donor and/or the sample collected from the donor can be confirmed to be good. On the other hand, when the relative expression levels in the cell population comprising mesenchymal stem cells deviate from the indices, the cell population contained in the sample collected from the donor is highly likely to cause cell aggregation, and thus, the cell aggregation can be reduced by properly changing culture conditions (change of an inoculation density, a medium, a growth factor, serum, etc.). In addition, when the relative expression levels in the cell population comprising mesenchymal stem cells deviate from the indices, cell aggregation can be reduced by separating a cell population comprising mesenchymal stem cells satisfying the indices through the use of, for example, a cell sorting technique, and inoculating and culturing the mesenchymal stem cells in the cell population. At the early stage of culture, culture conditions (change of an inoculation density, a medium, a growth factor, serum, etc.) may be designed such that the indices are satisfied at the final stage of the step, and thus, the indices may be satisfied at least at the final stage. In confirming the quality of a sample collected from a donor, a method for preparing and treating the sample, and a method for culturing a cell population are not particularly limited, and any method can be employed.

In the present invention, an optimal enzymatic treatment condition can be determined and/or predicted by measuring the relative expression level of COL11A1 gene to the expression level of SDHA gene, and the relative expression level of COL16A1 gene to the expression level of SDHA gene in a cell population obtained by enzymatically treating a sample collected from a donor, and evaluating by using as indices a condition that the cell population satisfies the relative expression level of COL11A1 gene to the expression level of SDHA gene of 6.0 or less and the relative expression level of COL16A1 gene to the expression level of SDHA gene of 1.5 or less. When a cell population comprising mesenchymal stem cells that satisfy the indices is obtained (preferably, easily obtained), the enzymatic treatment method can be determined and/or predicted to be appropriate for the sample collected from a donor. On the other hand, when a culture state continues with a value deviating from the indices, the enzymatic treatment method can be determined and/or predicted to be inappropriate for the sample collected from a donor. In determining and/or predicting an optimal enzymatic treatment method, a method for preparing and treating the sample, and a method for culturing a cell population are not particularly limited, and any method can be employed.

The indices can be measured at a necessary timing. Examples of the timing include, but are not particularly limited to, immediately after separation of cells from a biological sample, during a culture step, after purification in the culture step, immediately after the Nth passage (N represents an integer of 1 or more), during maintenance culture, before cryopreservation, after thawing, before formulation, or after formulation.

[5] Pharmaceutical Composition

The cell population comprising mesenchymal stem cells according to the present invention can be used as a pharmaceutical composition. Specifically, the present invention provides a pharmaceutical composition comprising the cell population according to the present invention and a pharmaceutically acceptable vehicle.

The pharmaceutical composition of the present invention is preferably a liquid preparation, and more preferably an injectable liquid preparation.

The pharmaceutical composition of the present invention can be used as a cell therapy agent, for example, a therapeutic agent for intractable diseases.

The pharmaceutical composition of the present invention can be used as a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer. The disease can be treated by administering the pharmaceutical composition of the present invention to a treatment site in an amount whereby an effect can be measured.

The present invention provides the cell population comprising mesenchymal stem cells according to the present invention for use in a pharmaceutical composition.

The present invention provides the cell population comprising mesenchymal stem cells according to the present invention for use in a cell therapy agent.

The present invention provides the cell population comprising mesenchymal stem cells according to the present invention for use in the treatment of a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

The present invention provides the cell population comprising mesenchymal stem cells according to the present invention for use in the regeneration of cardiac muscle, the production of cardiac muscle cells, angiogenesis, the repair of a blood vessel, or the suppression of immune response by administration to a patient or a subject.

The present invention provides a method for transplanting cells to a patient or a subject, and a method for treating a disease in a patient or a subject, comprising a step of administering a therapeutically effective amount of the cell population comprising mesenchymal stem cells according to the present invention to the patient or the subject.

The present invention provides use of the cell population comprising mesenchymal stem cells according to the present invention for the manufacture of a pharmaceutical composition.

The present invention provides use of the cell population comprising mesenchymal stem cells according to the present invention for the manufacture of a cell therapy agent.

The present invention provides use of the cell population comprising mesenchymal stem cells according to the present invention for the manufacture of a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

The present invention provides use of the cell population comprising mesenchymal stem cells according to the present invention for the manufacture of a therapeutic agent necessary for the regeneration of cardiac muscle, the production of cardiac muscle cells, angiogenesis, the repair of a blood vessel, or the suppression of immune response by administration to a patient or a subject.

The pharmaceutical composition of the present invention may be obtained by diluting a cell population comprising mesenchymal stem cells with a pharmaceutically acceptable vehicle. The pharmaceutically acceptable vehicle is not particularly limited as long as it is a solution that can be administered to a patient or a subject. The pharmaceutically acceptable vehicle may be an infusion preparation, and examples thereof include, but are not limited to, water for injection, physiological saline, 5% glucose solution, Ringer's solution, lactated Ringer's solution, acetated Ringer's solution, bicarbonated Ringer's solution, amino acid solution, starter solution (Solution I), rehydration solution (Solution II), maintenance infusion (Solution III), postoperative recovery solution (Solution IV), and Plasma-Lyte A (registered trademark).

The "patient or subject" used herein is typically a human and may be other animals. Examples of other animals include, but are not limited to, mammals such as dogs, cats, cattle, horses, pigs, goats, sheep, monkeys (cynomolgus monkey, rhesus monkey, common marmoset and Japanese monkey), ferrets, rabbits and rodents (mouse, rat, Mongolian gerbil, guinea pig and hamster); birds such as chickens and quails.

The "immune-related disease" used herein is not particularly limited as long as it is a disease related to an immune responses of a patient or subject. Examples thereof include graft-versus-host disease (GVHD), inflammatory bowel diseases (IBD), Crohn's disease, ulcerative colitis, radiation enteritis, diabetes mellitus, systemic lupus erythematosus, collagen disease, mycosis fungoides, multiple sclerosis, psoriasis, autoimmune bullous disease, and rheumatoid arthritis.

The pharmaceutical composition of the present invention may comprise any component for use in the treatment of a patient or subject. Examples of the component include, but are not limited to, salts, polysaccharides (e.g., hydroxyethyl starch (HES) and dextran), proteins (e.g., albumin), DMSO, amino acids, and medium components (e.g., components contained in RPMI1640 medium).

The pharmaceutical composition of the present invention may comprise various additives for increasing the preservation stability, the isotonicity, the absorbability, and/or the viscosity, such as an emulsifier, a dispersant, a buffer, a preservative, a wetting agent, an antioxidant, a chelating agent, a thickener, a gelling agent and a pH adjuster. Examples of the thickener include, but are not limited to, HES, dextran, methylcellulose, xanthan gum, carboxymethylcellulose and hydroxypropyl methylcellulose. The concentration of the thickener can be optionally set according to the selected thickener, within the range of concentration that is safe when administered to the patient or the subject and achieves the desired viscosity.

The pH of the pharmaceutical composition of the present invention can be adjusted to around neutral pH, for example, pH 6.5 or more or pH 7.0 or more, and/or pH 8.5 or lower or pH 8.0 or lower, but not limited thereto.

The pharmaceutical composition of the present invention is preferably a liquid preparation, and more preferably an injectable liquid preparation. As the injectable liquid preparation, liquid preparations suitable for injection are known in, for example, International Publication No. WO 2011/043136 and JP Patent Publication (Kokai) No. 2013-256510. The pharmaceutical composition of the present invention may also be an injectable liquid preparation described in the above literatures.

In addition, according to one aspect of the present invention, the pharmaceutical composition of the present invention may be used as a transplant preparation of a cell aggregate or sheet-like structure, or a gel preparation mixed with any gel, for the purpose of treating other diseases.

The dose of the pharmaceutical composition of the present invention is the amount of cells that allows a patient or a subject to whom the pharmaceutical composition has been administered to obtain therapeutic effects, compared with a patient or a subject to whom the pharmaceutical composition has not been administered. A specific dose can be appropriately determined depending on the form of administration, the administration method, the intended use, the age, body weight, symptoms of a patient or subject, and the like. A single dose of mesenchymal stem cells to a human is not particularly limited and is, for example, $10^4$ cells/kg body weight or more, $10^5$ cells/kg body weight or more or $10^6$ cells/kg body weight or more. Also, a single dose of mesenchymal stem cells to a human is not particularly limited and is, for example, $10^9$ cells/kg body weight or less, $10^8$ cells/kg body weight or less or $10^7$ cells/kg body weight or less.

Examples of the administration method of the pharmaceutical composition of the present invention include, but are not particularly limited to, subcutaneous injection, intralymph nodal injection, intravenous injection, intra-arterial injection, intraperitoneal injection, intrathoracic injection, direct localized injection, and direct localized transplantation. Regarding the administration method of the pharmaceutical composition of the present invention, intravenous injection, intravenous drip injection, local direct injection, local direct transplantation and others are known in, for example, JP Patent Publication (Kokai) No. 2015-61520, Onken J E, et al., American College of Gastroenterology Conference 2006 Las Vegas, Nev., Abstract 121., and Garcia-Olmo D, et al., Dis Colon Rectum 2005; 48: 1416-23. The pharmaceutical composition of the present invention can also be administered by various methods described in the above literatures.

The pharmaceutical composition of the present invention can be preserved in a frozen state until immediately before use. The temperature for cryopreservation is preferably −30° C. or lower, −40° C. or lower, −50° C. or lower, −80° C. or lower, −90° C. or lower, −100° C. or lower, −150° C. or lower, −180° C. or lower or −196° C. (liquid nitrogen temperature) or lower. When the pharmaceutical composition of the present invention is administered to a patient or subject, it can be used after being quickly thawed at 37° C.

The present invention will be specifically explained with reference to the Examples below; however, the present invention is not limited to the Examples.

EXAMPLES

Comparative Example 1

(Step 1: Collection of Amnion)

A fetal membrane and a placenta, which are fetal appendages, were aseptically collected from a pregnant woman (donor) of an elective cesarean section case after obtaining informed consent. The obtained fetal membrane and placenta were contained in a sterile tray containing physiological saline. An amnion was manually separated from the stump of the fetal membrane. The amnion was washed with a Hank's balanced salt solution (free of Ca and Mg) to remove attached blood and clots.

(Step 2: Enzymatic Treatment of Amnion and Collection of Amniotic MSCs)

The amnion was enzymatically treated by immersing the amnion comprising an epithelial cell layer and an extracellular matrix layer in a Hank's balanced salt solution (containing Ca and Mg) containing 300 PU/mL collagenase and 200 PU/mL dispase I, and shaking and stirring under conditions of 37° C., 90 minutes, and 50 rpm. The solution after enzymatic treatment was filtered through a nylon mesh having openings of 95 μm to remove undigested products of the amnion so as to collect a cell suspension containing amniotic MSCs. The obtained cell suspension was analyzed for the proportion of cells positive for the expression of CD90, which is one of surface antigens known as a typical positive marker of MSCs, using a flow cytometer. It was then confirmed that amniotic MSCs were able to be separated with high purity from the amnion.

The surface antigen analysis employed BD Accuri™ C6 Flow Cytometer from Becton, Dickinson (BD) and Company, and the measurement conditions involved analyzed cell number: 10,000 cells and flow rate setting: Slow (14 µL/min). FITC Mouse Anti-Human CD90 (BD/model number: 561969) was used as the antibody against the CD90 antigen, and FITC Mouse IgG1, K Isotype Control (BD/model number: 349041) was used as the antibody for isotype control.

(Step 3: Cryopreservation of Amniotic MSCs)

The cell population obtained in the above section "Step2: Enzymatic treatment of amnion and collection of amniotic MSCs" was suspended in BAMBANKER (LYMPHOTEC Inc.) so as to be $1.0 \times 10^1$ cells/mL and then aliquoted into cryotubes. The cryotube was placed in a BICELL (freezing container) (NIHON FREEZER Co., Ltd.) and stored at −80° C. for 12 hours, and thereafter, cryopreserved at a liquid nitrogen temperature.

(Step 4: Culture of Amniotic MSCs)

The cell population obtained in the above section "Step 3: Cryopreservation of amniotic MSCs" was inoculated to an uncoated plastic culture vessel, and adherent cultured in αMEM (Alpha Modification of Minimum Essential Medium Eagle) containing 10% fetal bovine serum (FBS) (inactivated) and 1× Antibiotic-Antimycotic (manufactured by Thermo Fisher Scientific Inc.) until subconfluence. Thereafter, cells were dissociated using TrypLE Select (1×) (manufactured by Thermo Fisher Scientific Inc.), a ¼ amount of cells was inoculated to an uncoated plastic culture vessel at the same scale as that of the preceding culture and thereby subcultured. Medium replacement was carried out with a frequency of twice a week. Thus the subculture was continued.

Example 1

(Step 1: Collection of Amnion)

An amnion was obtained in the same manner as in Step 1 of Comparative Example 1 except that a fetal membrane and a placenta, which are fetal appendages, were aseptically collected from a donor different from the donor of Comparative Example 1.

(Step 2: Enzymatic Treatment of Amnion and Collection of Amniotic MSCs)

A cell suspension comprising amniotic MSCs was collected by the same method as in Step 2 of Comparative Example 1. The obtained cell suspension was analyzed in the same manner as in Comparative Example 1 for the proportion of cells positive for the expression of CD90, which is one of surface antigens known as a typical positive marker of MSCs, using a flow cytometer. It was confirmed that amniotic MSCs were able to be separated with high purity from the amnion.

(Step 3: Cryopreservation of Amniotic MSCs)

The cell population obtained in the above section "Step 2: Enzymatic treatment of amnion and collection of amniotic MSCs" was cryopreserved by the same method as in Step 3 of Comparative Example 1.

(Step 4: Culture of Amniotic MSCs)

The cell population obtained in the above section "Step 3: Cryopreservation of amniotic MSCs" was adherent cultured by the same method as in Step 4 of Comparative Example 1 until subconfluence. Subculture was performed by the same method as in Step 4 of Comparative Example 1.

<Analysis of CDH6 Expression>

For the cell populations of the 6th passage cultured in Comparative Example 1 and Example 1, the proportions of cells positive for CDH6 were measured using a flow cytometer.

In this measurement, used were Anti-CDH6-Mouse Mono IgG1 (R&D Systems Inc./model number: MAB2715) as a primary antibody against CDH6 antigen; Mouse Mono IgG1 (R&D Systems Inc./model number: MAB002) as an isotype control antibody; and Mouse F(ab)2 IgG (H+L) APC-conjugated Antibody (R&D Systems Inc./model number: F0101B) as a secondary antibody against the primary antibody against CDH6 antigen and the isotype control antibody thereof.

Figure 2:
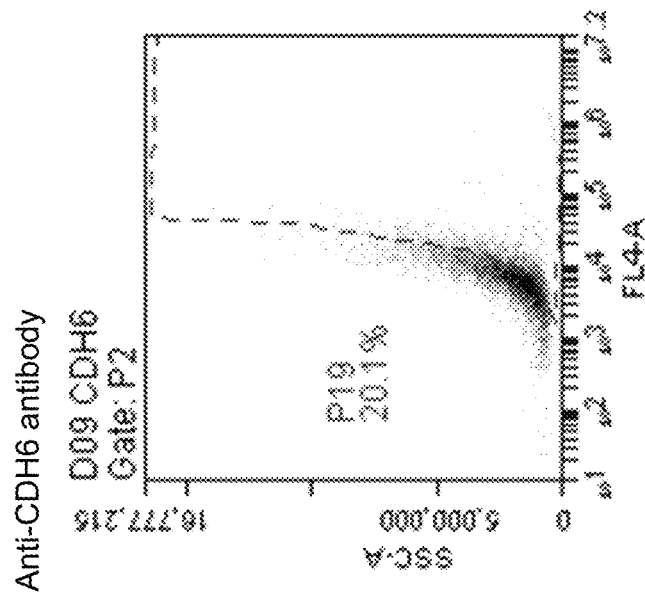
FIG. 2 shows results of measuring proportions of cells being positive for CDH6 by using a flow cytometer, for amniotic MSCs cultured in Comparative Example 1.
Figure 2:
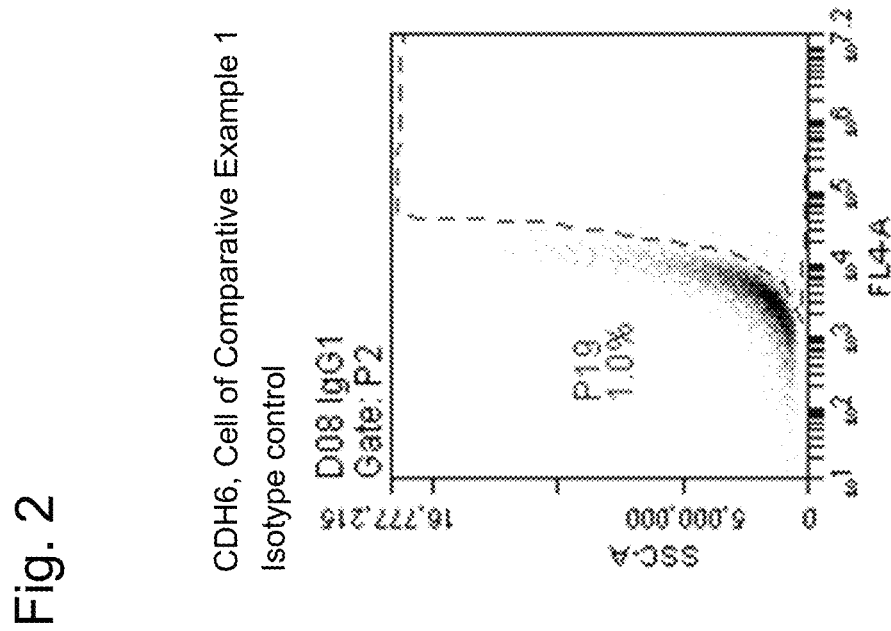

Analysis results are shown in FIGS. 1 and 2. In comparison with the cell population of Comparative Example 1, the positive rate of CDH6 was improved in the cell population of Example 1. In addition, the proportion of CDH6-positive mesenchymal stem cells was less than 30% (specifically 20.1%) in the cell population of Comparative Example 1, while the proportion of CDH6-positive mesenchymal stem cells was 30% or more (specifically 40.2%) in the cell population of Example 1.

<Analysis of Gene Expression>

The cell populations of the 6th passage cultured in Comparative Example 1 and Example 1 were analyzed by microarray analysis for the expression of VCAN gene, DCN gene, LUM gene, GPC4 gene, COL11A1 gene, COL16A1 gene, COL4A5 gene and SDHA gene.

The microarray analysis was carried out by the following procedures (1) to (5). The following procedures (3) to (5) were entrusted to and performed by RIKEN GENESIS CO., LTD.

(1) The cell populations of the 6th passage cultured in Comparative Example 1 and Example 1 were dissociated from plastic culture vessels using Cell Scraper (manufacture by Corning Inc.), and were collected by centrifugation.

(2) RNAlater (manufactured by Thermo Fisher Scientific Inc.) was added to the obtained cell pellets to stably store RNA, and then, using RNeasy Plus Mini Kit (manufactured by QIAGEN), total RNA was extracted and purified.

(3) cDNA was synthesized by a reverse transcription from 100 ng of total RNA. Then, cDNA was transcribed into cRNA by in vitro transcription with biotin labeling (using 3' IVT PLUS Reagent Kit).

(4) 10.0 µg of the labeled cRNA was added to a hybridization buffer and subjected to hybridization on Human GeneGenome U133A 2.0 Array (manufactured by Affymetrix, Inc.) for 16 hours, followed by washing with GeneChip Fluidics Station 450 (manufactured by Affymetrix, Inc.), staining with phycoerythrin, scanning using GeneChip Scanner 3000 7G (manufactured by Affymetrix, Inc.), image analysis using AGCC (Affymetrix GeneChip Command Console Software) (manufactured by Affymetrix, Inc.), and then quantification using Affymetrix Expression Console (manufactured by Affymetrix, Inc.).

(5) Numerical data files were analyzed using the analysis software GeneSpring GX (manufactured by Agilent Technologies, Inc.).

The expression level of each gene was determined as the relative expression level to the expression level of the SDHA gene. Results are shown in the following table.

TABLE 1

|  |  | COL11A1 | COL16A1 | COL4A5 | VCAM | DCN | LUM | GPC4 |
|---|---|---|---|---|---|---|---|---|
| Cell population of Example 1 | Fluorescence intensity | 1055.7 | 592.1 | 167.4 | 3554.3 | 1827.0 | 2208.7 | 104.1 |
|  | Relative expression level* | 1.1 | 0.6 | 0.2 | 3.6 | 1.9 | 2.2 | 0.1 |
| Cell population of Comparative Example 1 | Fluorescence intensity | 9135.5 | 2136.3 | 656.8 | 7602.6 | 5243.0 | 8647.6 | 1144.8 |
|  | Relative expression level* | 8.7 | 2.0 | 0.6 | 7.2 | 5.0 | 8.2 | 1.1 |

*Relative expression level of each gene to the expression level of SDHA gene

From Table 1, it was found that the relative expression levels of COL11A1 gene and COL16A1 gene were lower in the cell population of Example 1 in comparison with the cell population of Comparative Example 1. Specifically, it was found that in the cell population of Example 1 the relative expression level of COL11A1 gene to the expression level of SDHA gene was 6.0 or less and the relative expression level of COL16A1 gene to the expression level of SDHA gene was 1.5 or less. On the other hand, it was found that in the cell population of Comparative Example 1 the relative expression level of COL11A1 gene to the expression level of SDHA gene was larger than 6.0 and the relative expression level of COL16A1 gene to the expression level of SDHA gene was larger than 1.5.

In addition, from Table 1, it was found that the relative expression level of COL4A5 gene was lower in the cell population of Example 1 in comparison with the cell population of Comparative Example 1. Specifically, it was found that in the cell population of Example 1 the relative expression level of COL4A5 gene to the expression level of SDHA gene was 0.4 or less. On the other hand, it was found that in the cell population of Comparative Example 1 the relative expression level of COL4A5 gene to the expression level of SDHA gene was larger than 0.4.

In addition, from Table 1, it was found that the relative expression levels of VCAN gene, DCN gene and LUM gene were lower in the cell population of Example 1 in comparison with the cell population of Comparative Example 1. Specifically, it was found that in the cell population of Example 1 the relative expression level of VCAN gene to the expression level of SDHA gene was 6.0 or less; the relative expression level of DCN gene to the expression level of SDHA gene was 3.0 or less; and the relative expression level of LUM gene to the expression level of SDHA gene was 6.0 or less. On the other hand, it was found that in the cell population of Comparative Example 1 the relative expression level of VCAN gene to the expression level of SDHA gene was larger than 6.0; the relative expression level of DCN gene to the expression level of SDHA gene was larger than 3.0; and the relative expression level of LUM gene to the expression level of SDHA gene was larger than 6.0.

In addition, from Table 1, it was found that the relative expression level of GPC4 gene was lower in the cell population of Example 1 in comparison with the cell population of Comparative Example 1. Specifically, it was found that in the cell population of Example 1 the relative expression level of GPC4 gene to the expression level of SDHA gene was 0.5 or less. On the other hand, it was found that in the cell population of Comparative Example 1 the relative expression level of GPC4 gene to the expression level of SDHA gene was larger than 0.5.

<Evaluation of Cell Aggregability>

The cell aggregability was evaluated by the following procedures (1) to (6).
(1) The cell populations of the 6th passage cultured in Comparative Example 1 and Example 1 were suspended so as to be $2.0 \times 10^5$ cells/mL in αMEM (Alpha Modification of Minimum Essential Medium Eagle) containing 10% fetal bovine serum (FBS) (inactivated) and 1× Antibiotic-Antimycotic (manufactured by Thermo Fisher Scientific Inc.), and thereby a cell suspension was prepared.
(2) 4 mL each of the prepared cell suspension was inoculated to a 6-well plate for suspension culture (Sumitomo Bakelite Co., Ltd./product number: MS-8006R).
(3) The 6-well plate for suspension culture was placed on a shaker for use in an incubator, Orbital Shaker OS-762 (Optima Inc.), and was subjected to gyratory culture (suspension culture) for 24 hours in the environment of a $CO_2$ concentration of 3% or higher and 5% or lower, and 37° C. under the condition of 90 rpm.
(4) The cell suspension obtained by gyratory culture was observed under a microscope, and formation of cell aggregates was confirmed. The cell suspension obtained by gyratory culture was collected and filtered by a cell strainer (35-μm nylon mesh filter) (Corning Inc./product number: 352235), and cell aggregates were trapped on a mesh.
(5) A non-filtered cell suspension (i.e., containing cell aggregates and single cells) and a cell suspension obtained by filtration (not containing cell aggregates) were stained with trypan blue, and cell counting was carried out using an automated cell counter, Countess II FL (Thermo Fisher Scientific Inc.).
(6) Cell aggregability was calculated by the following equation.

Cell aggregability (%)=100−(cell number per 1 mL of the cell suspension obtained by filtration/total number of cells per 1 mL of the non-filtered cell suspension)

Measurement results are shown in the following table.

TABLE 2

|  | Number of non-aggregated cells ($\times 10^5$ cells/mL) | Total number of cells ($\times 10^5$ cells/mL) | Cell aggregability (%) |
|---|---|---|---|
| Cell population of Example 1 | 4.1 | 7.9 | 47.7 |
| Cell population of Comparative Example 1 | 3.2 | 9.1 | 65.1 |

From Table 2, the cell aggregability of the cell population of Comparative Example 1 was 65.1% and the cell aggregability of the cell population of Example 1 was 47.7%. From the above, it was revealed that cell aggregability was lower in the cell population of Example 1 in comparison with the cell population of Comparative Example 1.

Thus, it was found that cell aggregability is low in the cell population having the following cell characteristic.

The cell population satisfies the relative expression level of COL11A1 gene to the expression level of SDHA gene of 6.0 or less and the relative expression level of COL16A1 gene to the expression level of SDHA gene of 1.5 or less.

Further, it was found that cell aggregability is low when a cell population satisfies the relative expression level of COL4A5 gene to the expression level of SDHA gene of 0.4 or less.

Further, it was found that cell aggregability is low when a cell population satisfies any one or more of: the relative expression level of VCAN gene to the expression level of SDHA gene of 6.0 or less; the relative expression level of DCN gene to the expression level of SDHA gene of 3.0 or less; and the relative expression level of LUM gene to the expression level of SDHA gene of 6.0 or less.

Further, it was found that cell aggregability is low when a cell population satisfies the relative expression level of GPC4 gene to the expression level of SDHA gene of 0.5 or less.

Thus, it was revealed that it is effective to satisfy at least the above condition (the relative expression level of COL11A1 gene to the expression level of SDHA gene of 6.0 or less and the relative expression level of COL16A1 gene to the expression level of SDHA gene of 1.5 or less) as the indices for obtaining a cell population having low cell aggregability, and that a cell population comprising mesenchymal stem cells having low cell aggregability can be obtained by using the above condition as indices. Therefore, by producing a cell preparation with a cell population comprising mesenchymal stem cells having low cell aggregability obtained by the present invention, a cell preparation with increased safety and reduced risk of causing an embolus can be produced.

Example 2

"Step 1: Collection of amnion", "Step 2: Enzymatic treatment of amnion and collection of amniotic MSCs", "Step 3: Cryopreservation of amniotic MSCs", and "Step 4: Culture of amniotic MSCs" were carried out in the same manner as in Example 1, from a pregnant woman of an elective cesarean section case after obtaining informed consent (a donor different from those of Comparative Example 1 and Example 1). A portion of the cell population of each passage was collected during culturing of the amniotic MSCs, and then each of the collected cell populations was evaluated for the conditions (a) and (b) below. The evaluation of the conditions was carried out using the same procedures as those of the above sections "Analysis of CDH6 expression" and "Analysis of gene expression".
(a) in the cell population, the proportion of CDH6-positive mesenchymal stem cells is 30% or more; and
(b) the cell population satisfies any one or more of: the relative expression level of VCAN gene to the expression level of SDHA gene of 6.0 or less; the relative expression level of DCN gene to the expression level of SDHA gene of 3.0 or less; and the relative expression level of LUM gene to the expression level of SDHA gene of 6.0 or less.

There were a cell population satisfying the conditions (a) and (b) and a cell population not satisfying them in collected cell populations. Therefore, these two types of cell populations were evaluated for cell aggregability by the same method as in "Evaluation of cell aggregability" described in paragraph 0153.

Evaluation results are shown in the following table.

TABLE 3

|  | Number of non-aggregated cells ($\times 10^5$ cells/mL) | Total number of cells ($\times 10^5$ cells/mL) | Cell aggregability (%) |
| --- | --- | --- | --- |
| Cell population satisfying conditions (a) and (b) | 4.2 | 7.4 | 43.7 |
| Cell population not satisfying conditions (a) and (b) | 2.3 | 7.4 | 69.0 |

From Table 3, the cell aggregability of the cell population not satisfying the conditions (a) and (b) was 69.0%, and the cell aggregability of the cell population satisfying the conditions (a) and (b) was 43.7%. Since cell aggregability is lower in the cell population satisfying the conditions (a) and (b) in comparison with the cell population not satisfying the conditions (a) and (b), a cell population having low cell aggregability can be selectively obtained by using the conditions (a) and (b) as indices.

In addition, the cell population satisfying the conditions (a) and (b) and the cell population not satisfying them were also evaluated for the following conditions (c) and (d).
(c) the cell population comprising mesenchymal stem cells satisfies the relative expression level of COL11A1 gene to the expression level of SDHA gene of 6.0 or less, and
(d) the relative expression level of COL16A1 gene to the expression level of SDHA gene of 1.5 or less.

The cell population satisfying the conditions (a) and (b) satisfied the conditions (c) and (d) while the cell population not satisfying the conditions (a) and (b) did not satisfy the conditions (c) and (d).

From the above, in a culture step, cell aggregability is lower in a cell population that satisfies the relative expression level of COL11A1 gene to the expression level of SDHA gene of 6.0 or less and the relative expression level of COL16A1 gene to the expression level of SDHA gene of 1.5 or less, compared to a cell population not satisfying the above conditions, and thus, the cell aggregability of mesenchymal stem cells can be evaluated by using the conditions as indices. In addition, a cell population having low cell aggregability can be selectively obtained by using the conditions as indices. Further, according to the present invention, changes in the cell aggregability of mesenchymal stem cells can be quickly known and predicted by measuring (or measuring over time) the indices. This enables production of a cell preparation useful for intravenous administration.

Example 3: Production of Pharmaceutical Composition

A portion of the cell population obtained in the above Example 1 is subjected to preparation of a pharmaceutical composition. A pharmaceutical composition (cell preparation) consisting of 20 mL of RPMI1640 medium containing $4.0 \times 10^8$ amniotic MSCs, 800 mg of HES, 0.7 mL of DMSO and 800 mg of human serum albumin is prepared. The pharmaceutical composition is enclosed in a freezing bag and stored in a frozen state. The pharmaceutical composition can be thawed upon use and applied to a patient.

Example 4

(Step 1: Collection of Amnion and Obtainment of Amniotic MSCs)

An amnion was obtained by the same method as in step 1 of Comparative Example 1, Example 1 and Example 2 except that a fetal membrane and a placenta, which are fetal appendages, were aseptically collected from two donors (donors X and Y), who are different from those of Comparative Example 1, Example 1 and Example 2. Amniotic MSCs obtained from fetal appendages of the two were referred to as #X and #Y, respectively.

Cell populations comprising amniotic MSCs of #X and #Y obtained in the above were cryopreserved by the same method as in step 3 of Comparative Example 1, Example 1 and Example 2, and cultured by the following method.

(Step 2: Culture of Amniotic MSCs)

The cell population obtained in the above was inoculated to an uncoated plastic culture vessel, and adherent cultured in αMEM containing 10% FBS and 1× Antibiotic-Antimycotic until subconfluence. The subculture was carried out by the same method as in step 4 of Comparative Example 1, Example 1 and Example 2.

(Gene Expression Analysis)

A portion of the cell population of the 6th passage obtained in the above "Step 2: Culture of amniotic MSCs" was collected and subjected to microarray analysis to confirm whether the following condition is satisfied, and at the same time, the remaining of the cell population was cryopreserved until results of microarray analysis were obtained.

The cell population comprising mesenchymal stem cells satisfies the relative expression level of COL11A1 gene to the expression level of SDHA gene of 6.0 or less and the relative expression level of COL16A1 gene to the expression level of SDHA gene of 1.5 or less.

(Gene Expression Analysis)

Analysis results on each gene in the cell population of the 6th passage are shown in Table 4.

As shown in Table 4, in the donor X-derived cell population, the relative expression level of COL11A1 gene to the expression level of SDHA gene was 2.6 and the relative expression level of COL16A1 gene to the expression level of SDHA gene was 0.4. Also, in the donor Y-derived cell population, the relative expression level of COL11A1 gene to the expression level of SDHA gene was 2.9 and the relative expression level of COL16A1 gene to the expression level of SDHA gene was 0.1.

Hence, it was found that in the cell populations derived from the donors X and Y the relative expression level of COL16A1 gene to the expression level of SDHA gene was 1.5 or less and the relative expression level of COL11A1 gene to the expression level of SDHA gene was 6.0 or less. Specifically, it was found that in the cell populations of the present Example the relative expression level of COL16A1 gene to the expression level of SDHA gene was 0.5 or less and the relative expression level of COL11A1 gene to the expression level of SDHA gene was 3.0 or less.

In addition, from Table 4, in the donor X-derived cell population, the relative expression level of VCAN gene to the expression level of SDHA gene was 5.5; the relative expression level of DCN gene to the expression level of SDHA gene was 2.0; and the relative expression level of LUM gene to the expression level of SDHA gene was 2.4. Further, in the donor Y-derived cell population, the relative expression level of VCAN gene to the expression level of SDHA gene was 4.9; the relative expression level of DCN gene to the expression level of SDHA gene was 2.3; and the relative expression level of LUM gene to the expression level of SDHA gene was 3.0.

Hence, it was found that in the cell populations derived from the donors X and Y, the relative expression level of VCAN gene to the expression level of SDHA gene was 6.0 or less; the relative expression level of DCN gene to the expression level of SDHA gene was 3.0 or less; and the relative expression level of LUM gene to the expression level of SDHA gene was 6.0 or less. Specifically, it was found that in the cell populations of the present Example the relative expression level of VCAN gene to the expression level of SDHA gene was 5.5 or less; the relative expression level of DCN gene to the expression level of SDHA gene was 2.5 or less; and the relative expression level of LUM gene to the expression level of SDHA gene was 4.0 or less.

Further, from Table 4, in the donor X-derived cell population, the relative expression level of GPC4 gene to the expression level of SDHA gene was 0.1. Also, in the donor Y-derived cell population, the relative expression level of GPC4 gene to the expression level of SDHA gene was 0.2.

Hence, it was found that in the cell populations derived from the donors X and Y the relative expression level of GPC4 gene to the expression level of SDHA gene was 0.5 or less. Specifically, it was found that in the cell population of the present Example the relative expression level of GPC4 gene was 0.3 or less.

From the above, it was confirmed that a cell population having the above cell characteristics can be obtained also in cell populations obtained from donors different from those of Comparative Example 1, Example 1 and Example 2. Since Examples 1 and 2 showed that cell aggregability is low in the cell populations having the above cell characteristics, it can be inferred that cell aggregability is low also in the cell populations obtained in the present Example (Example 4).

The invention claimed is:

1. A cell population comprising mesenchymal stem cells, the cell population having the following cell characteristics:

TABLE 4

| | | COL11A1 | COL16A1 | VCAN | DCN | LUM | GPC4 |
|---|---|---|---|---|---|---|---|
| Cell population of donor X | Fluorescence intensity | 2629.7 | 419.5 | 5555.8 | 2064.08 | 2467.6 | 90.5 |
| | Relative expression level* | 2.6 | 0.4 | 5.5 | 2.0 | 2.4 | 0.1 |
| Cell population of donor Y | Fluorescence intensity | 2745.7 | 110.5 | 4681.7 | 2181.9 | 2850.0 | 182.9 |
| | Relative expression level* | 2.9 | 0.1 | 4.9 | 2.3 | 3.0 | 0.2 |

*Relative expression level of each gene to the expression level of SDHA gene the cell population satisfies the relative expression level of COL11A1 gene to the expression level of SDHA gene of 6.0 or less and the relative expression level of COL16A1 gene to the expression level of SDHA gene of 1.5 or less.

2. The cell population of claim 1, wherein the cell population is a cultured or cryopreserved cell population.

3. The cell population of claim 1, wherein the cell population further has the following cell characteristics: the cell population satisfies the relative expression level of COL4A5 gene to the expression level of SDHA gene of 0.4 or less.

4. The cell population of claim 1, wherein the cell population further has the following cell characteristics: the cell population satisfies any one or more of: the relative expression level of VCAN gene to the expression level of SDHA gene of 6.0 or less; the relative expression level of DCN gene to the expression level of SDHA gene of 3.0 or less; and the relative expression level of LUM gene to the expression level of SDHA gene of 6.0 or less.

5. The cell population of claim 1, wherein the cell population further has the following cell characteristics: the cell population satisfies the relative expression level of GPC4 gene to the expression level of SDHA gene of 0.5 or less.

6. The cell population of claim 1, wherein the proportion of CDH6-positive mesenchymal stem cells is 30% or more in the cell population.

7. The cell population of claim 1, wherein the mesenchymal stem cells are derived from a fetal appendage.

8. The cell population of claim 1, wherein the cell population has a low cell aggregability.

9. The cell population of claim 1, wherein the cell population can be cultured up to 40 days or later after start of an in vitro culture.

10. A pharmaceutical composition comprising the cell population of claim 1, and a pharmaceutically acceptable vehicle.

\* \* \* \* \*